(12) United States Patent
Madamsetty et al.

(10) Patent No.: US 10,611,796 B2
(45) Date of Patent: Apr. 7, 2020

(54) METHOD FOR REGRESSING PANCREATIC TUMOR BY A LIPOSOMAL FORMULATION ALONG WITH DNA VACCINES

(71) Applicants: COUNCIL OF SCIENTIFIC & INDUSTRIAL RESEARCH, New Delhi (IN); MAYO CLINIC, Rochester, MN (US)

(72) Inventors: Vijay Sagar Madamsetty, Telangna (IN); Arabinda Chaudhuri, Telangna (IN); Debabrata Mukhopadhyay, Jacksonville, FL (US)

(73) Assignees: COUNCIL OF SCIENTIFIC & INDUSTRIAL RESEARCH, New Delhi (IN); MAYO CLINIC, Rochester, MN (US)

(*) Notice: Subject to any disclaimer, the term of this patent is extended or adjusted under 35 U.S.C. 154(b) by 79 days.

(21) Appl. No.: 15/460,701

(22) Filed: Mar. 16, 2017

(65) Prior Publication Data
US 2017/0267719 A1 Sep. 21, 2017

(30) Foreign Application Priority Data
Mar. 16, 2016 (IN) .............................. 201611009088

(51) Int. Cl.
| | | |
|---|---|---|
| *A61K 31/12* | (2006.01) | |
| *A61K 31/7068* | (2006.01) | |
| *A61K 39/00* | (2006.01) | |
| *A61K 45/06* | (2006.01) | |
| *C07K 7/06* | (2006.01) | |
| *A61K 9/127* | (2006.01) | |
| *A61K 9/00* | (2006.01) | |

(52) U.S. Cl.
CPC .............. *C07K 7/06* (2013.01); *A61K 9/0019* (2013.01); *A61K 9/127* (2013.01); *A61K 31/12* (2013.01); *A61K 31/7068* (2013.01); *A61K 39/0011* (2013.01); *A61K 2039/5154* (2013.01); *A61K 2039/53* (2013.01); *A61K 2039/55555* (2013.01); *A61K 2039/6018* (2013.01)

(58) Field of Classification Search
None
See application file for complete search history.

(56) References Cited

U.S. PATENT DOCUMENTS

| | | | |
|---|---|---|---|
| 2008/0102110 A1 | 5/2008 | Lee et al. | |
| 2011/0182814 A1* | 7/2011 | Kelly ..................... | A61K 47/64 424/9.1 |
| 2012/0219499 A1 | 8/2012 | Kelly | |

FOREIGN PATENT DOCUMENTS

| | | |
|---|---|---|
| IN | 0017/DEL/2013 | 1/2013 |
| IN | 2170/DEL/2010 | 9/2014 |
| WO | 2009/129220 | 10/2009 |
| WO | 2011/057078 | 5/2011 |
| WO | 2012/035557 | 3/2012 |
| WO | 2014/106856 | 7/2014 |

OTHER PUBLICATIONS

Pancreatic Cancer, Merck Manual, Jan. 2017, pp. 1-5 accessed Mar. 12, 2017 at URL merckmanuals.com/professional/gastrointestinal-disorders/ (Year: 2017).*
Bausch et al., "Plectin-1 is a Biomarker of Malignant Pancreatic Intraductal Papillary Mucinous Neoplasms,"J Gastrointest Surg 13: 1948-1954 (2009) (Year: 2009).*
Yamasaki et al., "Intravenous genetic mesothelin vaccine based on human adenovirus 40 inhibits growth and metastasis of pancreatic cancer," Int'l J. Cancer 133:88-97 (2013) (Year: 2013).*
Jemal et al., "Cancer Statistics", CA Cancer J Clin, vol. 57, No. 1, pp. 43-66, Jan./Feb. 2007.
Shukla et al., "Selective delivery of therapeutic agents for the diagnosis and treatment of cancer", Expert Opin. Biol. Ther. vol. 6, No. 1, pp. 39-54 (2006).
Kelly et al., "Targeted Nanoparticles for Imaging Incipient Pancreatic Ductal Adenocarcinoma", PLoS Medicine, vol. 5, issue 4, Apr. 2008.
Vyas et al., "Ligand-Receptor-Mediated Drug Delivery: An Emerging Paradigm in Cellular Drug Targeting", Critical Reviews in Therapeutic Drug Carrier Systems, vol. 18, No. 1, pp. 1-76 (2001).
Yu et al., "Targeted Drug Delivery in Pancreatic Cancer", Biochim Biophys Acta., 1805(1): 97, pp. 1-16, Jan. 2010.

(Continued)

*Primary Examiner* — Julie Ha
*Assistant Examiner* — Kristina M Hellman
(74) *Attorney, Agent, or Firm* — Hamre, Schumann, Mueller & Larson, P.C.

(57) ABSTRACT

The present invention discloses a Plectin-1 receptor targeting novel cationic KTLLPTPK(SEQ ID NO: 1)-lipopeptide. The present invention further discloses a liposomal formulation comprising the cationic KTLLPTPK(SEQ ID NO: 1)-lipopeptide, at least two co-lipids, a therapeutic agent, and a pharmaceutically acceptable carrier. The present invention also provides a method for regressing established pancreatic tumors comprising administering a therapeutically effective amount of the liposomal formulation with the therapeutic agents in combination with targeted genetic immunization (DNA vaccination) i.e. by immunizing mice with electrostatic complexes (direct in-vivo DC-targeting cationic liposomes) of DNA vaccines encoding mesothelin (p-CMV-MSLN).

1 Claim, 11 Drawing Sheets
Specification includes a Sequence Listing.

(56) References Cited

OTHER PUBLICATIONS

Bausch et al., "Plectin-1 as a novel biomarker for pancreatic cancer", Clin Cancer Res.. 17(2): 302-309, pp. 1-15, Jan. 15, 2011.
Ishii et al., "TANK-binding kinase-1 delineates innate and adaptive immune responses to DNA vaccines", Nature, vol. 451, pp. 725-729, Feb. 7, 2008.
Gurunathan et al., "DNA Vaccines: Immunology, Application, and Optimization*", Annu. Rev. Immunol. 18:927-974 (2000).
Sallusto et al., "Dendritic Cells Use Macropinocytosis and the Mannose Receptor to Concentrate Macromolecules in the Major Histocompatibility Complex Class II Compartment: Downregulation by Cytokines and Bacterial Products", J. Exp. Med., vol. 182, pp. 389-400, Aug. 1995.
Lu et al., "Development of an antigen-presenting cell-targeted DNA vaccine against melanoma by mannosylated liposomes", Biomaterials 28, pp. 3255-3262 (2007).
Jiang et al., "Galactosylated liposome as a dendritic cell-targeted mucosal vaccine for inducing protective anti-tumor Immunity", Acta Biomaterialia 11, pp. 356-367 (2015).
Wijagkanalan et al., "Efficient targeting to alveolar macrophages by intratracheal administration of mannosylated liposomes in rats", Journal of Controlled Release 125, pp. 121-130, Oct. 2007.
Srinivas et al., "Cationic Amphiphile with Shikimic Acid Headgroup Shows More Systemic Promise Than Its Mannosyl Analogue as DNA Vaccine Carrier in Dendritic Cell Based Genetic Immunization", J. Med. Chem. 53, pp. 1387-1391 (2010).
Srinivas et al., "A long-lasting dendritic cell DNA vaccination system using lysinylated amphiphiles with mannose-mimicking head-groups", Biomaterials 33, pp. 6220-6229 (2012).
Un et al., "Development of an ultrasound-responsive and mannose-modified gene carrier for DNA vaccine therapy", Biomaterials 31, pp. 7813-7826 (2010).
Un et al., "Suppression of Melanoma Growth and Metastasis by DNA Vaccination Using an Ultrasound-Responsive and Mannose-Modified Gene Carrier", Molecular Pharmaceuticals 8, pp. 543-554 (2011).
Szakács et al., "Targeting multidrug resistance in cancer", Nature Reviews, vol. 5, pp. 219-234 (2006).
Kelly et al., "Mesothelin targeted agents in clinical trials and in preclinical development", Mol Cancer Ther., vol. 11, No. 3, pp. 517-525, Mar. 2012.
Garu et al., "Genetic Immunization With In Vivo Dendritic Cell-targeting Liposomal DNA Vaccine Carrier Induces Long-lasting Antitumor Immune Response", Molecular Therapy vol. 24 No. 2, pp. 385-397, Feb. 2016.

\* cited by examiner

Cationic KTLLPTPK-lipopeptide 1

Cationic SNLHPSDK-lipopeptide 2

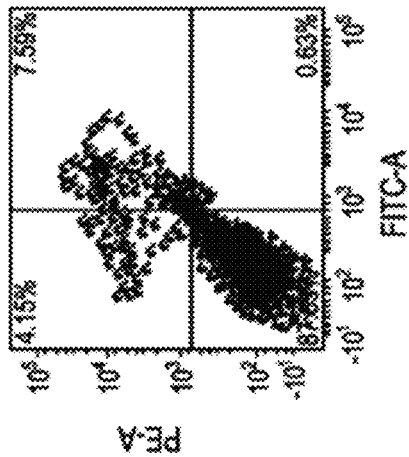
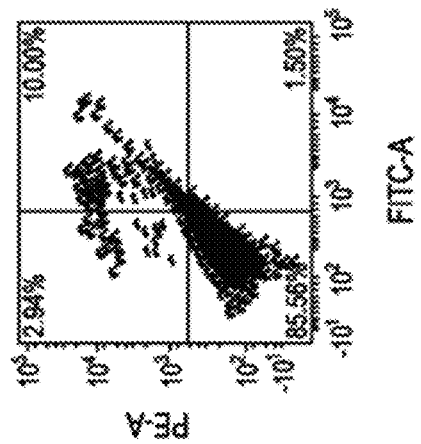
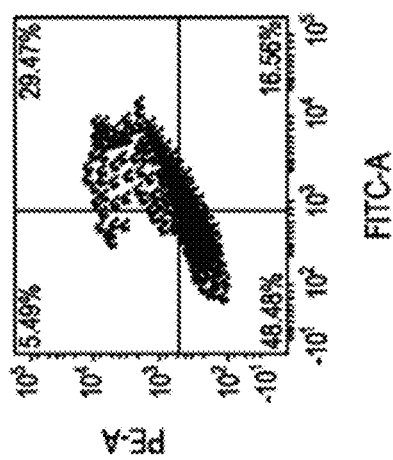
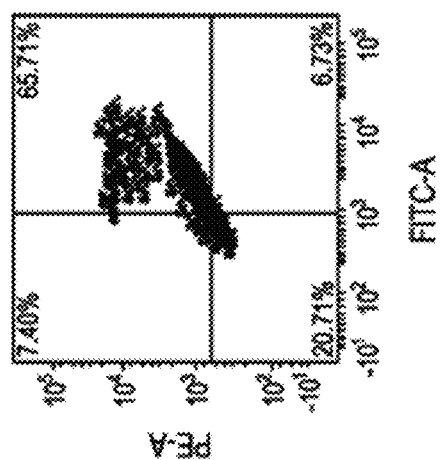
Fig. 4C
Fig. 4D
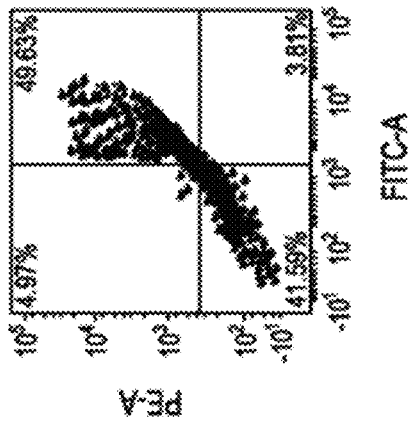
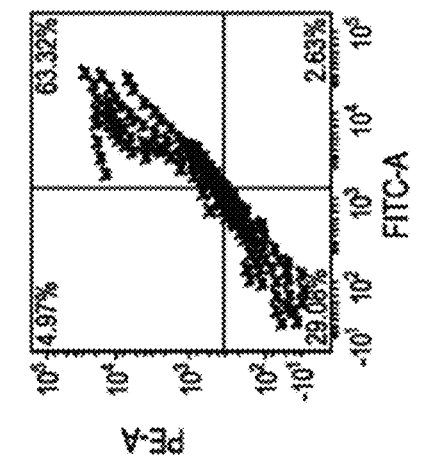

SEQUENCE LISTING

<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: Octapeptide of the present application

<400> SEQUENCE: 1

Lys Thr Leu Leu Pro Thr Pro Lys
1               5

```
<210> SEQ ID NO 2
<211> LENGTH: 8
<212> TYPE: PRT
<213> ORGANISM: Artificial Sequence
<220> FEATURE:
<223> OTHER INFORMATION: Non-targeting octapeptide

<400> SEQUENCE: 2

Ser Asn Leu His Pro Ser Asp Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Amino acid sequnce of Plectin 1 targeting
      peptide

<400> SEQUENCE: 3

Lys Thr Leu Leu Pro Thr Pro
1               5

<210> SEQ ID NO 4
<211> LENGTH: 7
<212> TYPE: PRT
<213> ORGANISM: Artificial Sequence
<220> FEATURE:
<223> OTHER INFORMATION: non-targeting amino acid sequence

<400> SEQUENCE: 4

Ser Asn Leu His Pro Ser Asp
1               5

<210> SEQ ID NO 5
<211> LENGTH: 16
<212> TYPE: PRT
<213> ORGANISM: Artificial Sequence
<220> FEATURE:
<223> OTHER INFORMATION: multimeric synthetic peptide

<400> SEQUENCE: 5

Ala Lys Thr Leu Leu Pro Thr Pro Gly Gly Ser Lys Lys Lys Lys Ala
1               5                   10                  15

<210> SEQ ID NO 6
<211> LENGTH: 4
<212> TYPE: PRT
<213> ORGANISM: Artificial Sequence
<220> FEATURE:
<223> OTHER INFORMATION: synthetic peptide

<400> SEQUENCE: 6

Asp Ser Pro Glu
1
```

METHOD FOR REGRESSING PANCREATIC TUMOR BY A LIPOSOMAL FORMULATION ALONG WITH DNA VACCINES

FIELD OF THE INVENTION

The present invention relates to novel liposomal formulation comprising of cationic lipopeptides having a KTLLPTPK(SEQ ID NO: 1)-octapeptide head-group, two co-lipids, and therapeutic agents for regressing established pancreatic tumor. The present invention also embodies a combination approach in which the above mentioned liposomal formulations of KTLLPTPK(SEQ ID NO: 1)-lipopeptides with entrapped therapeutics and a previously developed in vivo dendritic cell targeting DNA vaccine carriers encoding mesothelin (p-CMV-MSLN) are used simultaneously for regressing established orthotopic mouse pancreatic tumor.

BACKGROUND AND PRIOR ART OF THE INVENTION

Pancreatic cancer is one of the most difficult cancers to combat with less than 5% 5 year survival and less than 1 year median survival rates [Xu, J. et al. Cancer statistics, 2007. CA Cancer J Clin 57:43-66]. Despite intense global efforts, curing this dreaded disease remains a formidable challenge. Recent studies using genetically engineered mouse model revealed Plectin-1 (Plec1) as a potential novel imaging biomarker for pancreatic duct adeno carcinoma PDAC. Effective diagnosis and treatment of cancer critically depends on developing tumor or tumor vasculature specific delivery of diagnostic markers/cytotoxic cancer drugs (Shukla, G. S. et al. Expert. Opin. Biol. Ther. 2006; 6:39-54). To this end, potent cytotoxic drugs are often selectively delivered to tumor cells or tumor endothelial cells via receptors over expressed on tumors/tumor vasculatures (Vyas, S. P. et al. Crit. Rev. Ther. Drug Carrier Syst. 2001; 18:1-76). Prior studies reported that KTLLPTP(SEQ ID NO: 3) is a high affinity ligand for Plec1 [Kelly et al. (2008) Targeted nanoparticle for imaging incipient pancreatic ductal adenocarcinoma. PLoS Med 5:4:e85; Interactional Pat. Pub. No. WO 2009/129220, Kelly et al., published Oct. 22, 2009; WO2011057078-A2; WO2011057078-A3; CA2779730-A1; AU2010315021-A1; ~US2012219499-A1; EP2496948-A2; KR2012101054-A; CN102762984-A; JP2013510094-W; WO2009129220-A2; ~WO2009129220-A3; EP2265630-A2; JP2011521897-W; US2011182814-A1; CA2758415-A1]. These latter inventions disclose compositions and methods useful for diagnostic and imaging techniques for detecting and localizing the biomarker Plectin-1. The inventions disclose multimeric peptide ligand complexes (ssAKTLLPTPGGS (PEG5000)) 4 KKKKDOT-AssA-NH2 ([(pAla-Lys-Thr-Leu-Leu-Pro-Thr-Pro-Gly-Gly-Ser-PEG5K) 2-Lys] 2-Lys-Lys (DOTA)-pAla-NH2 (SEQ ID NO: 5)) to which imaging agents and/or therapeutic agents were conjugated) for targeting to Plectin-1. Lee et al. disclosed methods for preparation of lipid-hydrophilic polymer-reactive functional group-peptide (DSPE(SEQ ID NO: 6)-PEG-octreotide) and delivering anticancer drugs to pancreatic tumor (US2008102110-A1; JP2008115147-A; TW200819137-A; TW362270-B1). Additional prior arts related to targeting drugs to pancreatic tumors include: Targeted Drug Delivery in Pancreatic Cancer by Yu et al. (Biochim Biophys Acta., 2010, 1805(1), 97-104) and Plectin-1 as a Novel Biomarker for Pancreatic Cancer by Bausch et al. (Clin Cancer Res; 17(2); 302-9).

Genetic immunization (DNA vaccination, the administration of tumor antigen encoded DNA) is an emerging therapeutic approach for treatment of cancer. This therapeutic modality is capable of inducing both humoral and cellular immune responses against tumor (Ishii, K. J. et al. Nature 2008; 451:725-729, Gurunathan, S. et al. Annu. Rev. Immunol. 2000; 18:927-974). Efficient DNA vaccination requires targeting DNA vaccines to recipients' antigen present cells (APCs). To this end, mannose receptor, a 180 kDa multi-domains unique transmembrane receptor over expressed on the cell surfaces of APCs (Sallusto, F. et al. J. Exp. Med. 1995; 182:389-400) are finding increasing exploitations (Lu, Y. et al. Biomaterials, 2007, 28, 3255-3262; P.-L. Jiang et al. Acta Biomaterialia 2015, 11, 356-367; Wijagkanalan, W. et al. J. Controlled. Release. 2008, 125, 121-130). Srinivas, R. et al. demonstrated for the first time that liposomes of cationic amphiphiles with mannose-mimicking quinoyl- and shikimoyl-head-groups can target DNA vaccines to APCs via mannose receptors more efficiently than their mannosyl counterparts (Srinivas, R. et al. J. Med. Chem. 2010; 53:1387-1391). Subsequently, Srinivas, R. et al. disclosed more efficacious mannose receptor specific lysinylated cationic amphiphiles with mannose-mimicking shikimoyl- and quinoyl-head-groups for use in ex vivo (outside the body cells) dendritic cell (DC, the most professional antigen presenting cells) transfection based genetic immunization (Srinivas, R. et al. Biomaterials 2012, 33, 6220-6229, International Patent Application No. PCT/IN2011/000629; Indian Patent Application No. 2170/DEL/2010). However, such ex vivo DC-transfection based DNA vaccination methods suffer from a number of time-consuming and cost-ineffective steps including painstaking isolation of autologous DCs, transfecting them ex vivo with tumor antigen encoded DNA vaccines and reimplanting the ex vivo transfected DCs back into the recipient's body. To this end, Hashida and coworkers reported development of mannose-receptor selective and ultrasound-responsive mannosylated liposomes for direct in vivo transduction of DCs in genetic immunization (Un K. et al. Biomaterials 2010; 31: 7813-7826; Un K. et al. Mol Pharm 2011; 8: 543-554). Garu, A. et al. has recently developed an efficient method for direct in vivo targeting of DNA vaccines using novel liposomal DNA vaccine carriers (Indian Patent Application No. 0017/DEL/2013). Although inhibiting growth of melanoma tumor in mice priorly immunized with such direct in vivo DC-targeting liposomal DNA vaccine formulation was possible, this approach failed to regress established tumor. Potent targeted cancer therapeutics is often associated with multi-drug resistance (MDR), acute toxicities, cumulative dose-limiting cytoxicity, etc. Thus, there is an urgent need to use combination of targeted chemotherapy and in vivo DC-targeted tumor antigen encoded DNA vaccination for regressing established tumors (Szakacs, G. et al. Nat. Rev. Drug Discov. 2006; 5:219-234).

OBJECTIVE OF THE INVENTION

The main objective of the present invention is to provide a novel liposomal formulation comprising a cationic lipopeptide having KTLLPTPK(SEQ ID NO: 1)-octa peptide head-group, two co-lipids, and therapeutic agents, selected from curcumin and gemcitabine.

Another object of the present invention is to provide a process for the synthesis of the Plectin-1 receptor targeting KTLLPTPK(SEQ ID NO: 1)-lipopeptide and non-targeting cationic lipopeptide having formula A and formula B, respectively.

Still another objective of the present invention is to provide a method for regressing established tumor by combining in vivo dendritic cell targeted DNA vaccination encoding mesothelin (p-CMV-MSLN) and cancer chemotherapy using the formulation as mentioned above.

SUMMARY OF THE INVENTION

The present invention provides a liposomal formulation comprising the cationic KTLLPTPK(SEQ ID NO: 1)-lipopeptide having formula A, two co-lipids, a pharmaceutically acceptable carrier and therapeutic agents, wherein the ratio of the said components is in the range of 0.5:1:0.25:0.02:1-10.

In an embodiment of the present invention, there is provided a liposomal formulation wherein the said formulation acted synergistically for regressing the pancreatic tumor, when applied simultaneously with in vivo dendritic cell targeted DNA vaccines encoding mesothelin (p-CMV-MSLN)

An embodiment of the present invention relates to targeting cationic KTLLPTPK(SEQ ID NO: 1) lipopeptide and non-targeting cationic lipopeptides SNLHPSDK(SEQ ID NO:2) having formula A and formula B, respectively wherein, KTLLPTP(SEQ ID NO: 3) is the amino acid sequence of the Plectin 1 targeting peptides and SNLHPSD(SEQ ID NO: 4)- is the non-targeting amino acid sequence present in the head-group region of the lipopeptides described herein; $R_1$ and $R_2$ are each independently selected from hydrogen or a lipophilic moiety containing eight to twenty four carbon atom selected from the group consisting of alkyl, mono-, di- and tri-unsaturated alkenyl, provided both R1 and $R_2$ are not hydrogen;

$R_3$ is selected from a group consisting of hydrogen, $C_1$-$C_5$ alkyl, hydroxyl, and $C_1$-$C_5$ amino-alkyl; and X is either chlorine or bromine.

An embodiment of the present invention provides a process for preparation of the cationic lipopeptide (Formula A), said process comprising the steps:
i. Coupling Fmoc-Pro-OH with H-Lys(BOC)-2-ClTrt resin using HBTU and DIPEA in DMF at room temperature for 1.5 hour to obtain an intermediate Formula A

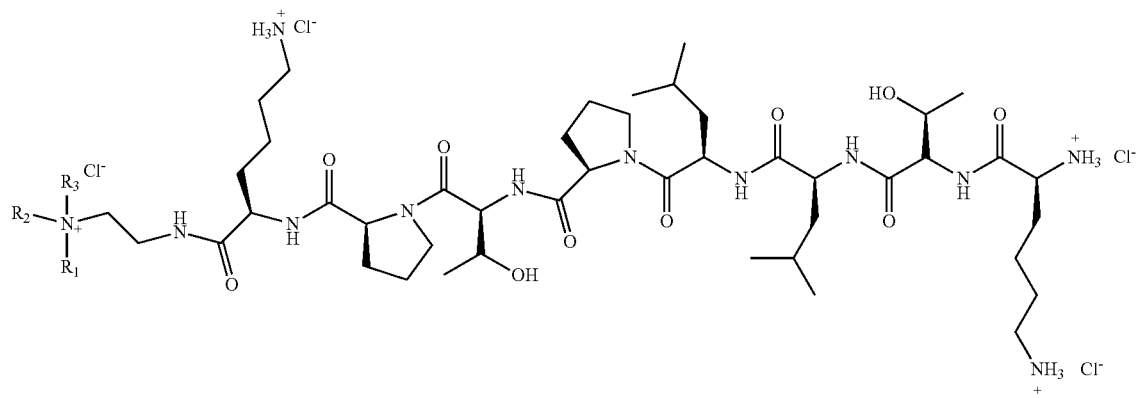

Formula B

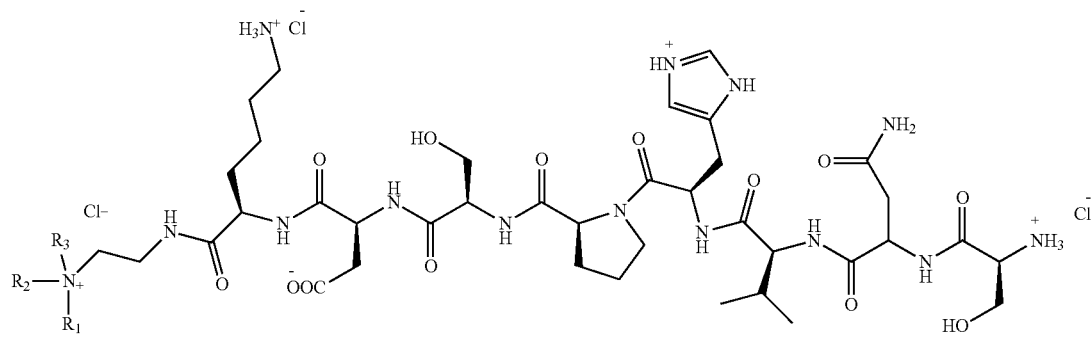

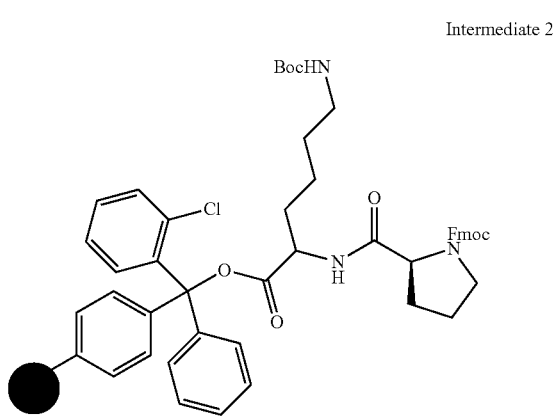

Intermediate 2 ii. Removing the Fmoc group from intermediate 2 by washing with piperidine in DMF at room temperature;
iii. Sequential couplings of Fmoc-Thr(O-tert-butyl)-OH, Fmoc-Pro-OH, Fmoc-Leu-OH, Fmoc-Leu-OH, Fmoc-Thr(O-tert-butyl)-OH and Boc-Lys(Boc)-OH using HATU (2 eqv.) and DIPEA (4 eqv.) to intermediate of step (ii) using the condition of step (i) to obtain a Octa-peptide intermediate 3;

v. Coupling the protected octa peptide intermediate 4 obtain in step (iv) with N, N-di-n-octadecyl-N-2-aminoethylamine in dry DCM to obtain a protected KTLLPTPK(SEQ ID NO: 1)-lipopeptide;

vi. Deprotecting the KTLLPTPK(SEQ ID NO: 1)-lipopeptide obtained in step (v) with TFA-DCM (95:5, v/v) to obtain a deprotected KTLLPTPK(SEQ ID NO: 1)-lipopeptide; and vii. Purifying the KTLLPTPK(SEQ ID NO: 1)-lipopeptide obtained in step (vi) to obtain the KTLLPTPK (SEQ ID NO: 1) lipopeptide A.

An embodiment of the present invention provides a process for preparation of the control non-targeting lipopeptide (Formula B), said process comprising the steps:

i. Coupling Fmoc-Asp(O-tert-butyl)-OH with H-Lys(Boc)-2-ClTrt resin using HBTU and DIPEA in DMF at room temperature for 1.5 hour to obtain an intermediate 5

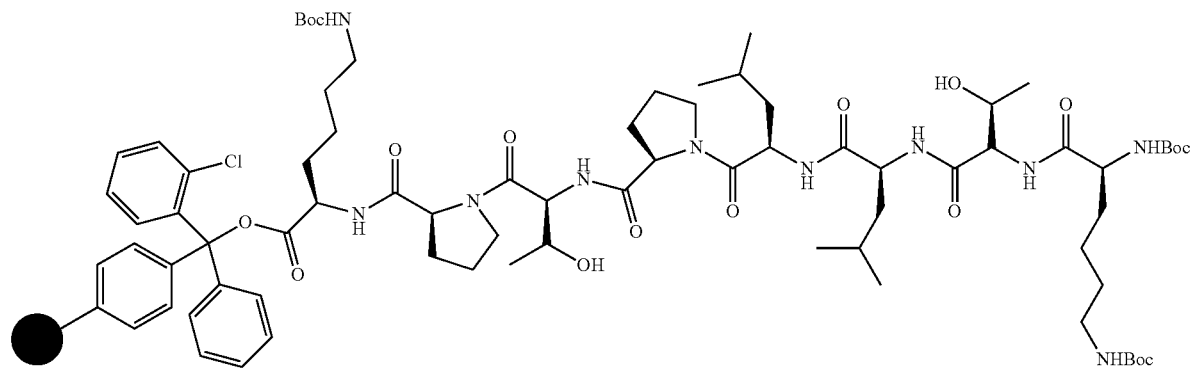

Octa peptide intermediate 3 iv. Removing the resin bound to octa peptide intermediate 3 obtained in step (iii) by treatment with TFA:DCM (0.5% v/v) for 2 h at 0° C. to obtain a protected octapeptide intermediate 4;

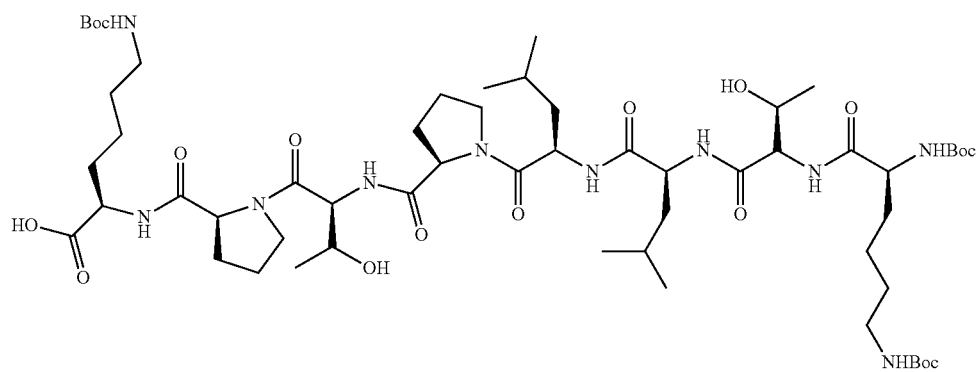

Octa peptide intermediate 4

Intermediate 5

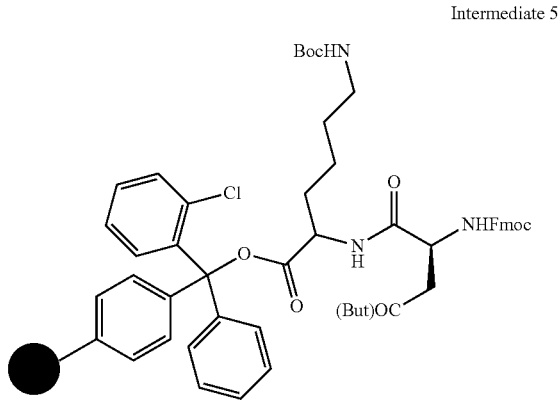

ii. Removing the Fmoc group from intermediate 5 by washing with piperidine in DMF at room temperature;
iii. Sequential couplings of Fmoc-Ser(O-tert-butyl)-OH, Fmoc-Pro-OH, Fmoc-His(Trt)-OH, Fmoc-Leu-OH, Fmoc-Asn(Trt)-OH and Boc-Ser(O-tert-butyl)-OH using HBTU (2 eqv.) and DIPEA (4 eqv.) to intermediate of step (ii) using the condition of step (i) to obtain a Octapeptide intermediate 6;

v. Coupling the protected octapeptide intermediate 7 obtain in step (iv) with N,N-di-n-octadecyl-N-2-aminoethylamine in dry DCM to obtain a protected SNLHPSDK(SEQ ID NO:2)-lipopeptide;
vi. Deprotecting the SNLHPSDK(SEQ ID NO:2)-lipopeptide obtained in step (v) with TFA-DCM-Triisopropylsilane (90:5:5, v/v) to obtain a deprotected SNLHPSDK(SEQ ID NO:2)-lipopeptide; and
vii. Purifying the SNLHPSDK(SEQ ID NO:2)-lipopeptide obtained in step (VI) to obtain the SNLHPSDK (SEQ ID NO:2) lipopeptide B.

H-Lys (BOC)-2-chloro trityl resin, all the amino acid derivatives used for Fmoc SPPS, HBTU and HOBt were purchased from NovaBiochem (Merck Millipore International, Darmstadt, Germany). Amberlyst IRA-400 resin and N, N-Diisopropylethylamine (both procured from Aldrich, USA). All reagents were purchased from local commercial suppliers and were used without further purification.

In an embodiment of the present invention, there is provided a liposomal formulation, wherein the co-lipids are selected from the group consisting of a neutral phosphatidyl ethanolamine, neutralphosphatidylcholine, phosphatidylphosphocholine, phosphatidylglycerol, DOPC cholesterol and DSPE(SEQ ID NO: 6)-(PEG)$_{2000}$-NH$_2$. (Avanti Polar, Alabama, USA) In an embodiment of the present invention, there is provided a liposomal formulation, wherein the

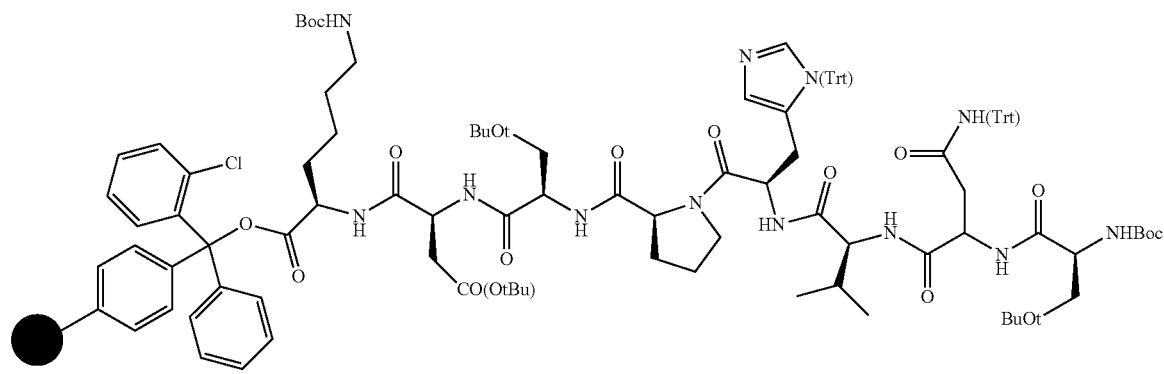

Octapeptide intermediate 6 iv. Removing the resin bound to octapeptide intermediate 6 obtained in step (iii) by treatment with TFA:DCM (0.5%, v/v) for 2 h at 0° C. to obtain a protected octapeptide intermediate 7;

pharmaceutically acceptable carrier is selected from the group consisting of di-oleoylphosphatidylcholine, di-stearoylphosphatidylcholine, dioleoylphospho ethanolamine.

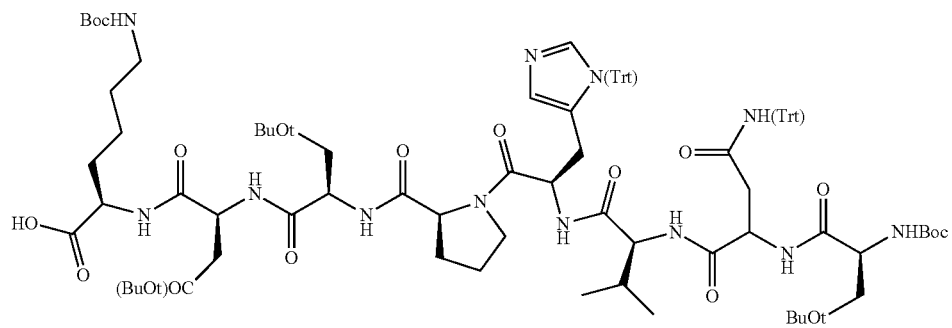

Octapeptide intermediate 7

In another embodiment of the present invention there is provided a liposomal formulation, wherein the therapeutic agent is selected from FDA approved specific drugs "gemcitabine" and another cyototoxic drug "curcumin" for pancreatic cancer, or a combination thereof.

In another embodiment of the present invention there is provided a liposomal formulation, wherein the weight ratio of curcumin (Sigma Aldrich, USA) and gemcitabine hydrochloride (Eli Lilly USA.) is in the range of 5-20:1-5 when used in combination.

In an embodiment of the present invention, a method of delivery of liposomal formulation selectively to pancreatic tumor cells and tumor endothelial cells comprising administering the liposomal formulation comprising the cationic KTLLPTPK(SEQ ID NO: 1)-lipopeptide having formula A, therapeutic agents and at least two co-lipids to a subject in need thereof.

In an embodiment of the present invention, a method of regressing pancreatic tumor, by combining cancer chemotherapy using the formulation (comprising the cationic KTLLPTPK(SEQ ID NO: 1)-lipopeptide formula A, therapeutic agents, at least two co-lipids) and in vivo dendritic cell targeted DNA vaccines, encoding mesothelin (p-CMV-MSLN) to a subject in need thereof.

BRIEF DESCRIPTION OF THE DRAWINGS

FIG. 3A shows a flow cytometry result of PANC-1 cells treated with Plectin 1 receptor targeting Rhodamine PE-labeled liposome. FIG. 3B shows a flow cytometry result of PANC-1 cells treated with non-targeting Rhodamine PE-labeled liposome. FIG. 3C shows a flow cytometry result of Pan02 cells treated with Plectin 1 receptor targeting Rhodamine PE-labeled liposome. FIG. 3D shows a flow cytometry result of Pan02 cells treated with non-targeting Rhodamine PE-labeled liposome. FIG. 3E shows a flow cytometry result of NIH3T3 cells treated with Plectin 1 receptor targeting Rhodamine PE-labeled liposome. FIG. 3F shows a flow cytometry result of PANC-1 cells treated with Rhodamine PE plectin-1 targeting-labeled liposome along with Plectin-1 antibody saturation.

FIGS. 4A-4E shows synergistic effects of liposomally encapsulated curcumin & gemcitabine in inducing apoptosis in PANC-1 (obtained from American type culture collection (ATCC, USA) Pan02 (murine pancreatic adenocarcinoma cells were procured from National Cancer Institute, NCI, USA) and NIH3T3 cells (purchased from National Centre for Cell Science, NCCS, Pune, India). FIG. 4A shows flow cytometer results of untreated PANC-1 (left chart), PAN02 (middle chart), and NIH3T3 (right chart), respectively, according to an embodiment. FIG. 4B shows flow cytometer results of PANC-1 (left chart), PAN02 (middle chart), and NIH3T3 (right chart) treated with curcumin in liposomes of KTLLPTPK(SEQ ID NO: 1)-lipopeptide 1, respectively, according to an embodiment. FIG. 4C shows flow cytometer results of PANC-1 (left chart), PAN02 (middle chart), and NIH3T3 (right chart) treated with gemcitabine encapsulate in liposomes of KTLLPTPK(SEQ ID NO: 1)-lipopeptide 1, respectively, according to an embodiment. FIG. 4D shows flow cytometer results of PANC-1 (left chart), PAN02 (middle chart), and NIH3T3 (right chart) treated with both curcumin and gemcitabine encapsulate in liposomes of KTLLPTPK(SEQ ID NO: 1)-lipopeptide 1, respectively, according to an embodiment. FIG. 4E shows flow cytometer results of PANC-1 (left chart), PAN02 (middle chart), and NIH3T3 (right chart) treated with both curcumin and gemcitabine encapsulate in a non-targeting control liposomes of SNLHPSDK(SEQ ID NO:2)-lipopeptide 2, respectively, according to an embodiment. Both untreated and treated cells were stained with FITC-Annexin V and Propidium iodide (PI) (both from Sigma, St. Louis, USA), for flow cytometric analysis. The horizontal and vertical axes represent cells labeled with FITC-Annexin V and PI, respectively in the dot plot. The FITC-Annexin V and PI are respectively detected by FITC channel and PE channel of a flow cytometry. Dots in the upper right quadrant represent late apoptotic cells (positive for both Annexin V and PI).

BRIEF DESCRIPTION OF SEQUENCE LISTING

Figure 1:
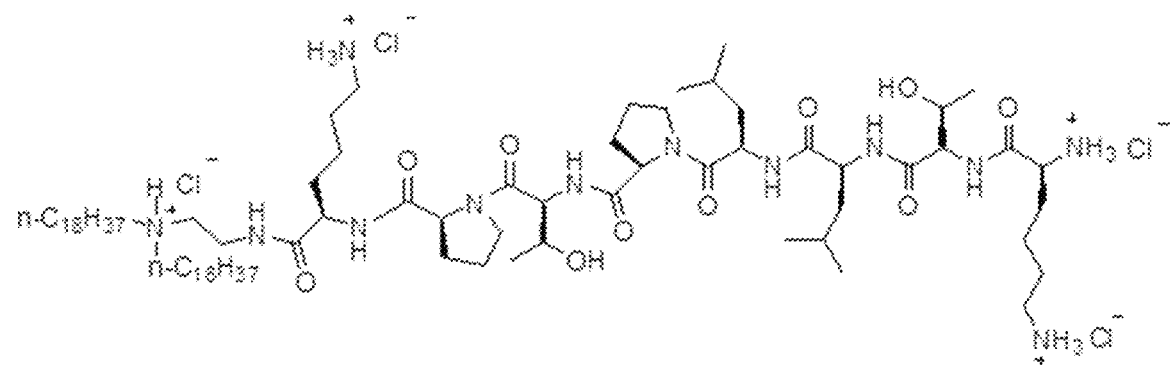
FIG. 1 shows structures of Plectin-1 Receptor targeting Cationic KTLLPTPK(SEQ ID NO: 1)-lipopeptide 1 and the non-targeting control cationic SNLHPSDK(SEQ ID NO:2)-lipopeptide 2.
Figure 1:
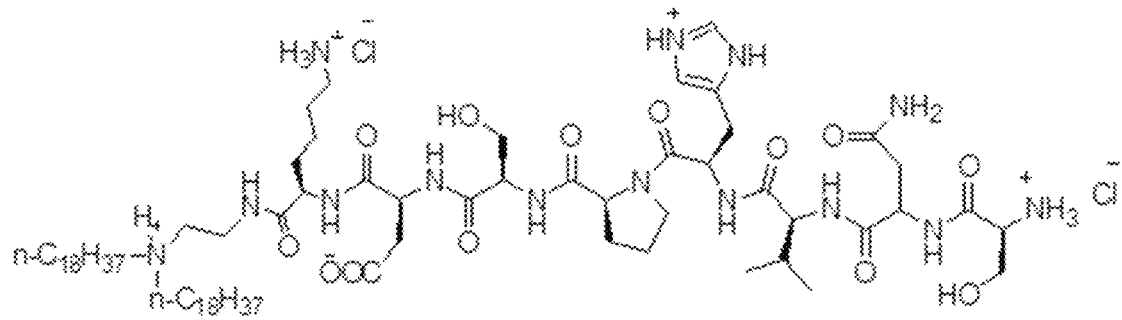

SEQ ID NO: 1. octapeptide of the present application (amino acid sequence)
SEQ ID NO: 2. non-targeting octapeptide (amino acid sequence)
SEQ ID NO: 3. Amino acid sequence of Plectin 1 targeting peptide (amino acid sequence)
SEQ ID NO: 4. non-targeting amino acid sequence (amino acid sequence)
SEQ ID NO: 5. multimeric synthetic peptide (amino acid sequence)
SEQ ID NO: 6. synthetic peptide (amino acid sequence)

Abbreviations

Pan02—Mouse pancreatic cancer cells
PANC-1—Human pancreatic cancer cells
C57BL/6J—is a common inbred strain of laboratory mouse
APC—Antigen presenting cells
MSLN—Mesothelin
IL—Interleukin
DC—Dendritic cell
DNA—Deoxyribonucleic acid
pCMV—plasmid cytomegalovirus
DOPC—1, 2-Dioleoyl-sn-glycero-3-phosphocholine
HATU—1-[Bis (dimethylamino) methylene]-1H-1, 2, 3-triazolo [4, 5-b] pyridinium 3-oxid hexafluorophosphate
HBTU—(2-(1H-benzotriazol-1-yl)-1, 1, 3, 3-tetramethyluronium hexafluorophosphate)
HOBT—Hydroxybenzotriazole
DIPEA—N, N-Diisopropylethylamine
EDCI—1-Ethyl-3-(3-dimethylaminopropyl) carbodiimide
TIS—Triisopropylsilane
TFA—Trifluoroacetic acid
DCM—Dichloromethane
DMEM—Dulbecco modified Eagle's minimal essential medium
FBS—Fetal bovine serum
RPMI-1640—Roswell Park Memorial Institute medium-1640
Plectin—1—cell membrane protein in pancreatic cancer cells
NIR Dye—Near Infra-Red Dye
HBSS—Hanks' Balanced Salt solution

DETAILED DESCRIPTION OF THE INVENTION

The present invention discloses that liposomes of lipopeptide containing pancreatic tumor homing peptide sequence KTLLPTP(SEQ ID NO:3)—can deliver potent cytotoxic drugs to pancreatic tumor cells via Plectin-1 receptor over expressed on pancreatic cancer cells.

The present invention discloses that intravenous administration of curcumin and gemcitabine both co-encapsulated in the liposomes of the KTLLPTPK(SEQ ID NO: 1)-lipopeptide A exhibits synergistic effect and inhibits pancreatic tumor growth significantly in a syngenic orthotopic mouse tumor model through apoptosis induction in tumor cells. The present invention also shows that the degree of tumor growth inhibition can be further enhanced with simultaneous use of in vivo dendritic cell targeted genetic immunization (DNA vaccination). An emerging approach for targeting tumor antigen encoded DNA vaccines to dendritic cells is based on exploiting mannose receptors over expressed on the surface of APCs (P. L. Jiang et al. *Acta Biomaterialia* 2015, 11, 356-367; Lu, Y. et al. *Biomaterials,* 2007, 28, 3255-3262; Wijagkanalan, W. et al. *J. Controlled. Release.* 2008, 125, 121-130; Un, K. et al. *Mol. Pharm.* 2011, 8, 543-554). To this end, prior studies showed that liposomal systems containing mannose-mimicking shikimoyl- and quinoyl-head-groups are more efficient in targeting DNA vaccines to dendritic cells under ex-vivo conditions (Srinivas, R. et al. *J Med. Chem.* 2010, 31, 1387-1391; Srinivas, R. et al. *Biomaterials* 2012, 33, 6220-6229). More recent work has disclosed development of liposomal systems for direct targeting of DNA vaccines to body's dendritic cells under in vivo conditions (i.e. without the need of isolating dendritic cells from the body as is done under ex vivo conditions). Liposome of lipid 1 is one such direct in vivo DC-targeting DNA vaccine carrier (WO 2014106856 A1, publication date: Jul. 10, 2014).

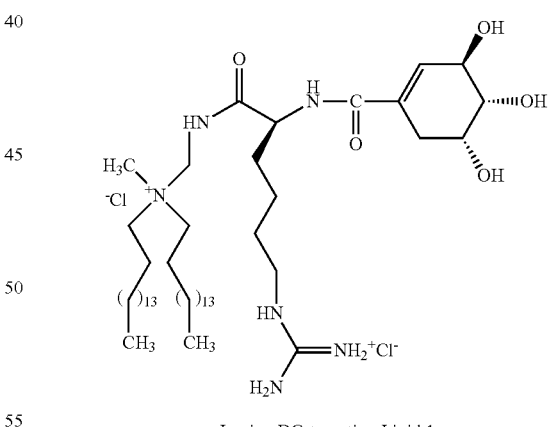

In vivo DC-targeting Lipid 1

The present invention discloses a combined therapeutic approach for combating pancreatic cancer by simultaneous applications of both the targeted chemotherapy and in vivo DC-targeted DNA vaccinations described above. In the targeted chemotherapy part of the present combination approach, pancreatic tumor targeting liposomes of KTLLPTPK(SEQ ID NO: 1)-lipopeptide A is used in delivering the liposomally co-encapsulated curcumin & gemcitabine. In the direct in vivo DC-targeted DNA vaccination part, p-CMV-MSLN DNA vaccines (encoding mesothelin, a 40-kDa membrane bound glycoprotein over expressed on the surface of pancreatic tumor cells, Kelly et al. Mol Cancer Ther. 2012, 11, 517-525) was targeted to DCs under in vivo conditions using in vivo DC-targeting liposomal DNA vaccine carriers described in WO 2014106856 A1. The present invention shows that simultaneous application of both these parts leads to significant regression of pancreatic tumor in orthotopic syngeneic mouse tumor model.

The present invention also relates to a process for the synthesis of the novel cationic lipopeptides with plectin-1 targeting KTLLPTP(SEQ ID NO: 3)-head-group and non-targeting control lipopeptide with SNLHPSD(SEQ ID NO: 4)-head group. The present invention further discloses plectin-1 receptor mediated drug delivery properties of the liposome of the cationic KTLLPTPK(SEQ ID NO: 1)-lipopeptide A. The novel structural features of the cationic lipopeptide with plectin-1 targeting KTLLPTP(SEQ ID NO:3)-head-group disclosed in the present invention include: (1) presence of hydrophobic groups which are directly linked to the positively charged nitrogen atom and (2) presence of plectin-1 receptor binding polar KTLLPTP (SEQ ID NO:3)-head-group covalently linked to the positively charged nitrogen atom via an additional lysine spacer in between the hydrophobic portion and plectin 1 targeting ligand. It is believed that this unique structural feature contributes significantly to drug delivery efficiency of the cationic lipopeptide containing the plectin-1 targeting KTLLPTP(SEQ ID NO: 3)-head-groups. According to the practice of the present invention, "cationic" means the positive charge is either on quaternized nitrogen or on a protonated nitrogen atom of the KTLLPTPK(SEQ ID NO: 1)-lipopeptide A. The cationic character of the present lipopeptide contributes to the enhanced interaction of the lipopeptide with biologically active molecules such as nucleic acids and/or with cell constituents such as negatively charged plasma membrane glycoproteins. Such enhanced interaction between the cationic lipopeptide and the therapeutically active biological macromolecules and/or cell membrane constituents plays a key role in successfully transporting the therapeutic molecules into the cells.

The general structures of cationic lipopeptides formulas A & B disclosed in the present invention are shown in FIG. 1.

Synthesis of KTLLPTPK(SEQ ID NO: 1)-Lipopeptide 1

Figure 2A:
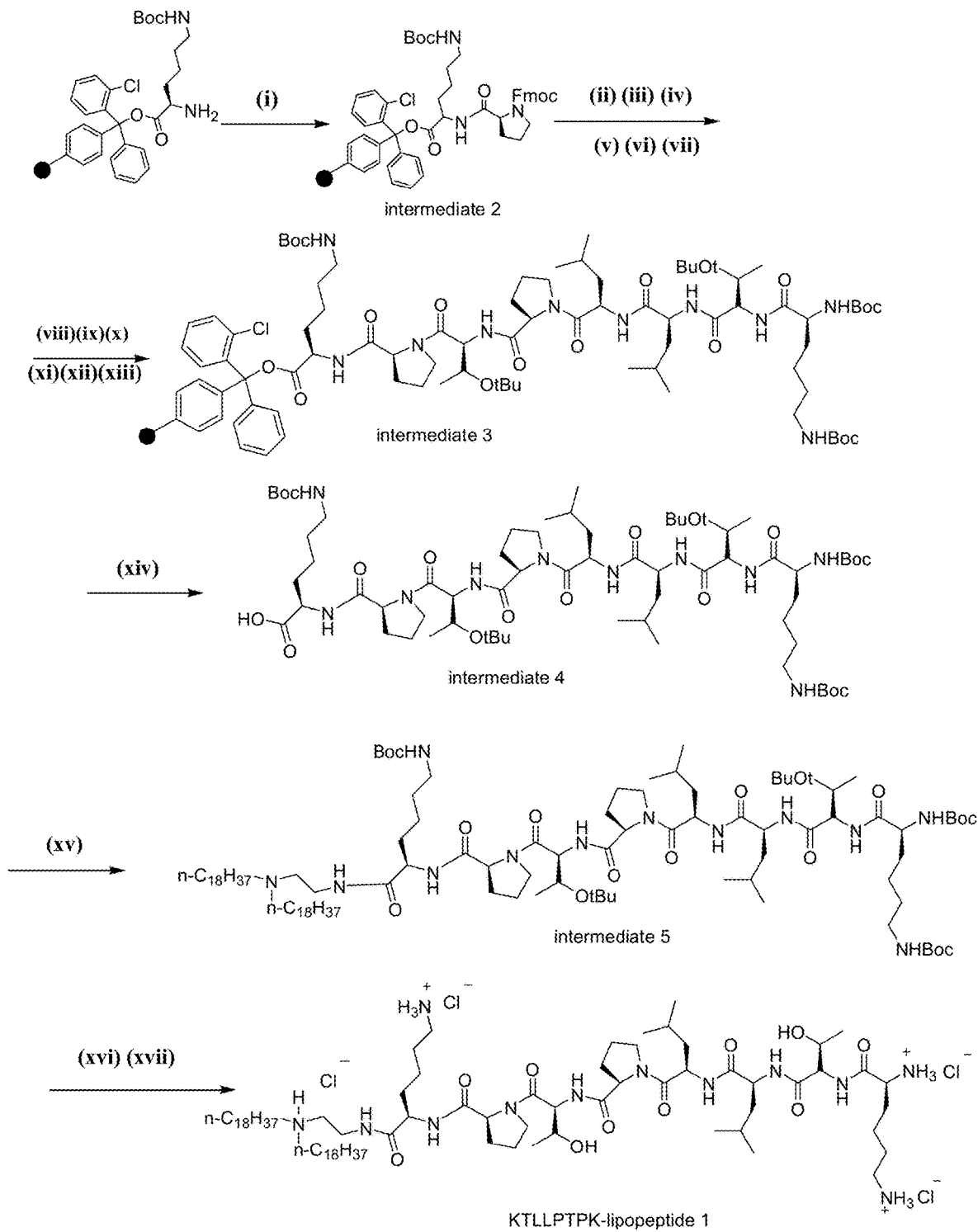
FIG. 2 (A) a schematic synthesis of Plectin-1 Receptor targeted Cationic KTLLPTPK(SEQ ID NO: 1)-lipopeptide-1 (B) non-targeting control cationic SNLHPSDK(SEQ ID NO:2)-Lipopeptide 2.

Synthetic strategies employed for preparing the cationic KTLLPTPK(SEQ ID NO: 1)-lipopeptides A are depicted schematically in Scheme 1 using KTLLPTPK(SEQ ID NO: 1)-lipopeptide 1 as an illustrative example. Scheme 1 (FIG. 2A) is a schematic representation of the Fmoc-strategy based solid phase peptide synthesis procedures used for the preparation of a representative cationic KTLLPTPK(SEQ ID NO: 1)-lipopeptide 1.

The Fmoc strategy based solid phase peptide synthesis route is used for preparing KTLLPTPK(SEQ ID NO: 1)-lipopeptide 1 (Scheme 1). H-Lys(Boc)-2-C1Trt resin (Ne-Boc-Lysine pre-loaded 2-chloro trityl resin, Scheme 1) is first swelled in solvent and then coupled with Fmoc-Pro-OH using HBTU and DIPEA to afford intermediate 2. The resin is then washed and the Fmoc group is removed with a solution of piperidine and DMF. Following the same Fmoc strategy, sequential couplings of Fmoc-Thr (O-tert-butyl)-OH, Fmoc-Pro-OH, Fmoc-Leu-OH, Fmoc-Leu-OH, Fmoc-Thr (O-tert-butyl)-OH and Boc-Lys (Boc)-OH using HBTU and DIPEA afford the resin associated octa-peptide intermediate 3. The resin-bound intermediate 3 is treated with very dilute solutions of TFA to obtain protected octapeptide intermediate 4 (Scheme 1). N, N-di-n-Octadecyl-N-2-aminoethylamine is coupled with protected octapeptide intermediate 4 to prepare the protected KTLLPTPK(SEQ ID NO: 1)-lipopeptide (Intermediate 5, Scheme 1). To remove the protecting groups of amino acids the intermediate 5 is treated with TFA: DCM (95:5, v/v). The deprotected lipopeptide is purified using acetone and dietheylether precipitation method. The precipitate upon chloride ion exchange chromatography over Amberlyst IRA-400 resin followed by purification with reversed phase HPLC affords the pure target KTLLPTPK(SEQ ID NO: 1)-lipopeptide 1 as a white, fluffy solid. The final KTLLPTPK(SEQ ID NO: 1)-lipopeptide is characterized by the molecular ion peak in ESIMS and purity is confirmed by reversed phase analytical HPLC using two different mobile phases.

Figure 2B:
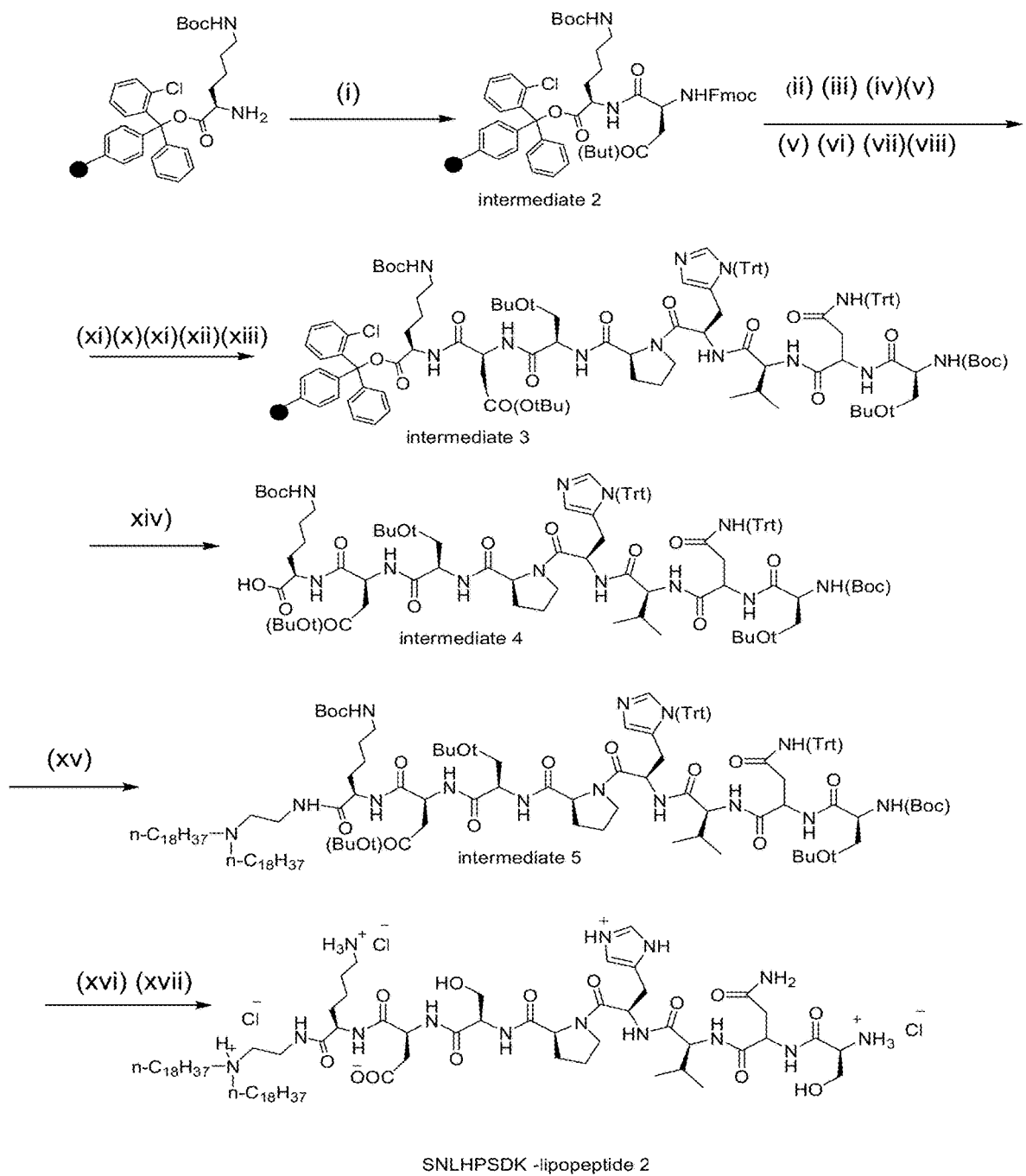

Synthesis of SNLHPSDK(SEQ ID NO:2)-Lipopeptide 2:

Synthetic strategies employed for preparing the cationic SNLHPSDK(SEQ ID NO:2)-lipopeptides B are depicted schematically in Scheme 2 (FIG. 2B) using SNLHPSDK (SEQ ID NO:2)-lipopeptide 2 as an illustrative example. Scheme 2 is a schematic representation of the Fmoc strategy based solid phase peptide synthesis procedures used for the preparation of a representative cationic SNLHPSDK(SEQ ID NO:2)-lipopeptide 2. H-Lys(Boc)-2-C1Trt resin-1 ($N^l$-Boc-Lysine pre-loaded 2-chloro trityl resin, Scheme 2) is first swelled in solvent and then coupled with Fmoc-Pro-OH using HBTU and DIPEA to afford intermediate 2. The resin is then washed and the Fmoc group is removed with a solution of piperidine and DMF. Following the same Fmoc strategy, sequential couplings of Fmoc-Asp (O-tert-butyl), Fmoc-Ser (O-tert-butyl), Fmoc-His (Trt), Fmoc-Leu-OH Fmoc-Asn (Trt)-OH, and Boc-Ser (O-tert-butyl), using HBTU and DIPEA affords the resin associated octa-peptide intermediate 3. The resin-bound intermediate 3 is treated with TFA:DCM (5:95, v/v) to obtain protected octa-peptide intermediate 4 (Scheme 2). N, N-di-n-Octadecyl-N-2-aminoethylamine is coupled with protected octapeptide intermediate 4 to prepare the protected SNLHPSDK(SEQ ID NO:2)-lipopeptide 2. To remove the protecting groups of amino acids the intermediate is treated with TFA:DCM:TIS (90:5:5, v/v). The deprotected lipopeptide is purified using Acetone and dietheylether precipitation method. The precipitate upon chloride ion exchange chromatography over Amberlyst IRA-400 resin followed by purification with reversed phase HPLC affords the pure non-targeting control SNLHPSDK(SEQ ID NO:2)-lipopeptide 2 as a white, solid. SNLHPSDK(SEQ ID NO:2)-lipopeptide 2 is characterized by the molecular ion peak in ESIMS and purity is confirmed by reversed phase analytical HPLC using two different mobile phases.

Formulations

The present invention provides a novel formulation comprising optimal amount of cationic lipopeptide with plectin-1-targeting KTLLPTPK(SEQ ID NO: 1)-head-groups and non-targeting control SNLHPSDK(SEQ ID NO:2)-lipopeptide 2, biological macromolecules and at least one co-lipid. One or more additional pharmaceutically acceptable substances can be included in the formulation of the present invention to stabilize the formulation for storage or to facilitate successful intracellular delivery of the biologically active molecules. Co-lipid of the present invention is useful for mixing with the cationic lipopeptide. Cholesterol is an excellent co-lipid for use in combination with the KTLLPTPK(SEQ ID NO: 1)-lipopeptide 1 or with the SNLHPSDK(SEQ ID NO:2)-lipopeptide 2 of the present invention to facilitate successful delivery of biologically active molecules in general, and curcumin and gemcitabine in particular, to tumor cells. A preferred molar ratio of the cationic KTLLPTPK(SEQ ID NO: 1)-lipopeptide, DOPC, cholesterol and DSPE(SEQ ID NO: 6)-(PEG)$_{2000}$-NH$_2$ in the formulation is 0.5:1:0.25:0.02. As such, it is within the art to vary the mole ratio of the KTLLPTPK(SEQ ID NO: 1)-lipopeptide 1, DOPC, cholesterol and DSPE(SEQ ID NO: 6)-(PEG)$_{2000}$-NH$_2$ to a considerably wide extent without compromising the therapeutic benefits of the present formulations. Typically, liposomes were prepared by dissolving the cationic KTLLPTPK(SEQ ID NO: 1)-lipopeptide 1 or non-targeting control SNLHPSDK(SEQ ID NO:2)-lipopeptide 2 and the co-lipids (cholesterol, DOPC and DSPE(SEQ ID NO: 6)-(PEG)$_{2000}$-NH$_2$) in the appropriate mole ratio in a mixture of methanol and chloroform in a glass vial. The solvent was then removed with a thin flow of moisture free nitrogen gas and the dried lipid film was kept under high vacuum for 8 h. The dried lipid film was hydrated in sterile deionized water in a total volume of 1 mL at cationic lipid concentration of 1 mM for a minimum of 12 h. Liposomes were then vortexed for 1-2 min to remove any adhering lipid film and sonicated in a bath sonicator (Ultrasonic 28X) for 2-3 min at room temperature to produce multilamellar vesicles (MLV). These MLVs were then sonicated with a Ti-probe (using a Branson 450 sonifier at 100% duty cycle and 25 W output power) for 1-2 min to produce small unilamellar vesicles (SUVs) as indicated by the formation of a clear translucent solution.

Figure 3:
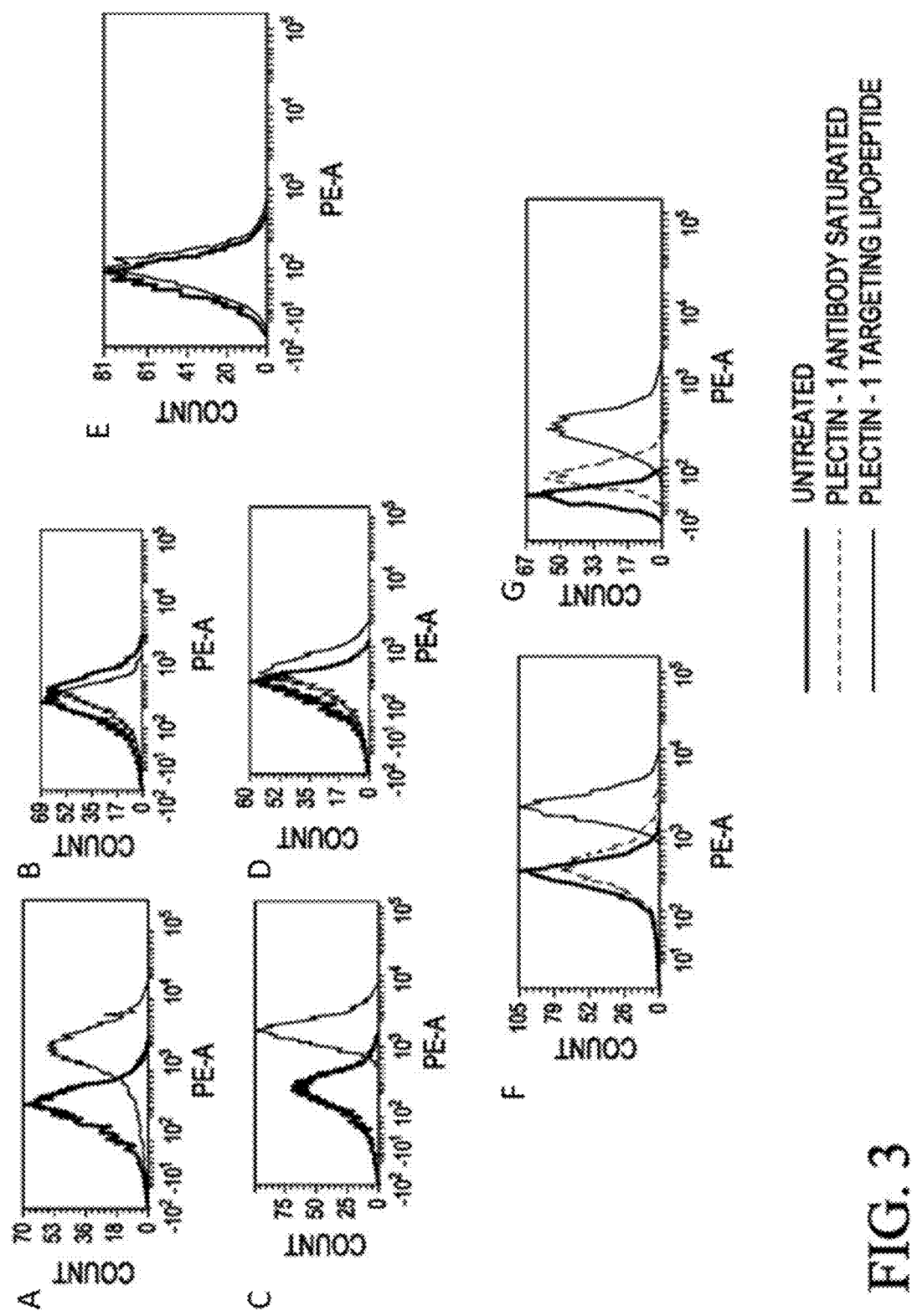
FIGS. 3A-3F show fluorescently labeled Rhodamine-PE encapsulated in liposomes of KTLLPTPK(SEQ ID NO: 1)-lipopeptide 1 enters pancreatic cancer cells via Plectin-1 receptor by a flow cytometry, according to an embodiment. The X-axis represents signal from PE Channel of the flow cytometry, as Rodhamine PE-labeled liposomes were used. This channel was used to determine the uptake of plectin 1 targeted liposomes in comparison with untreated samples. The Y-axis represents the Mean Fluorescence Intensity count. The thin curve indicated with "PLECTIN-1 TARGETING LIPOPEPTIDE" represents a curve of cells treated with Plectin 1 receptor targeting Rhodamine PE-labeled liposome, i.e., Rhodamine-PE encapsulated in liposomes of KTLLPTPK(SEQ ID NO: 1)-lipopeptide-1. The dotted curve indicated with "PLECTIN-1 ANTIBODY SATURATED" represents a curve of cells treated with Plectin 1 receptor targeting Rhodamine PE-labeled liposome after Plectin 1 antibody treatment for saturation of plectin-1 receptor. The thick curve indicated with "UNTREATED" represents the curve of untreated cells.
FIG. 3G shows a flow cytometry result of Pan02 cells treated with Plectin 1 receptor targeting Rhodamine PE-labeled liposome along with Plectin-1 antibody saturation. PANC-1 are human pancreatic cancer cells and plectin-1 positive cells. Pan02 are mouse pancreatic cancer cells and plectin-1 positive cells. NIH-3T3 cells are plectin-1 negative cells. Cellular uptake analyzed by FACS after 4 h of Rhodamine-PE encapsulated liposome addition of KTLLPTPK(SEQ ID NO: 1)-lipopeptide 1. Uptake of Rhodamine-PE encapsulated in liposomes of KTLLPTPK(SEQ ID NO: 1)-lipopeptide 1 can be mediated via Plectin-1 receptor in PANC-1 and Pan02 cells. Cells were pre-incubated with monoclonal antibody against plectin-1 then treated with Rhodamine-PE encapsulated in liposomes of KTLLPTPK (SEQ ID NO: 1)-lipopeptide-1 analyzed by Flow cytometric of both cells without antibody treatment and cells pre-treated with mAbs against plectin-1 was taken after 4 h of Rhodamine-PE liposome addition. No such cellular uptake was observed in NIH-3T3 cells in which expression level of plectin 1 receptor is poor (compared to that in pancreatic cancer cells).
Figure 4A:
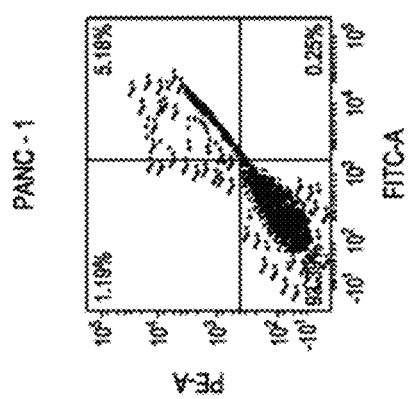
Figure 4A:
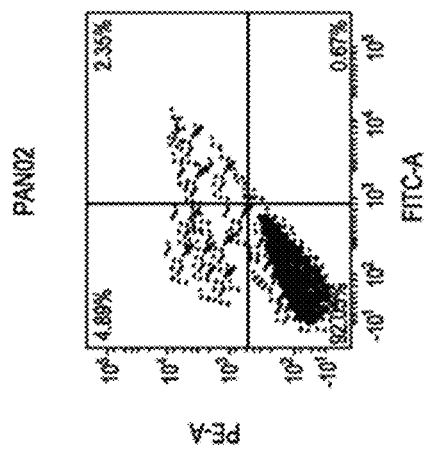
Figure 4A:
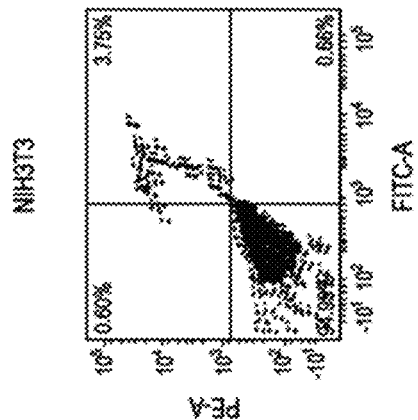
Figure 4A:
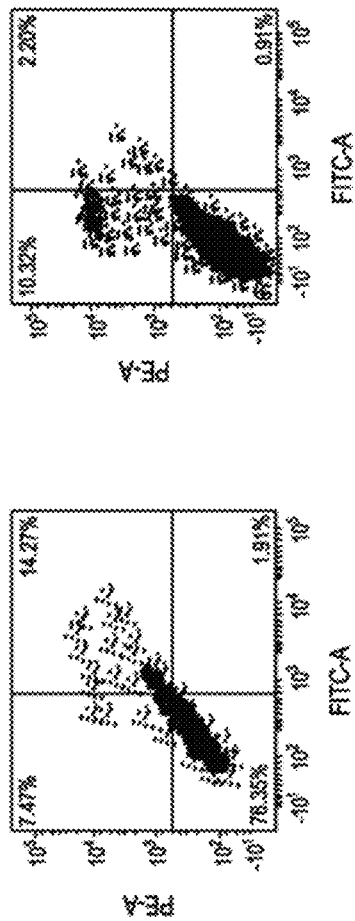
Figure 4B:
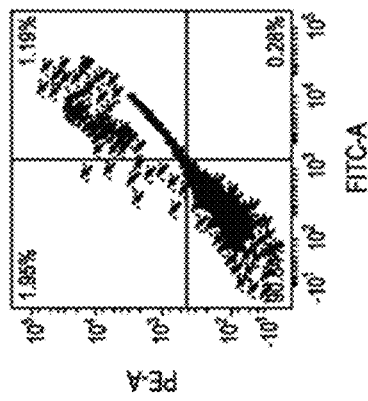
Figure 4E:
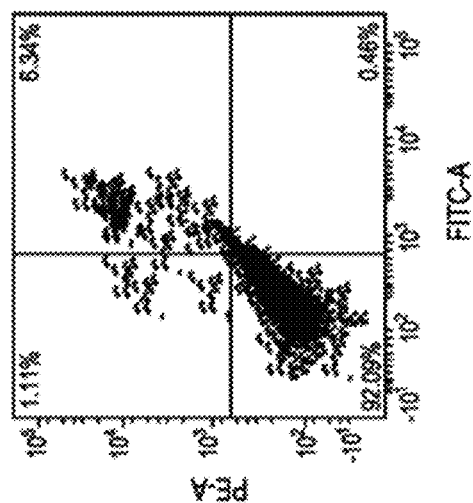
Figure 4E:
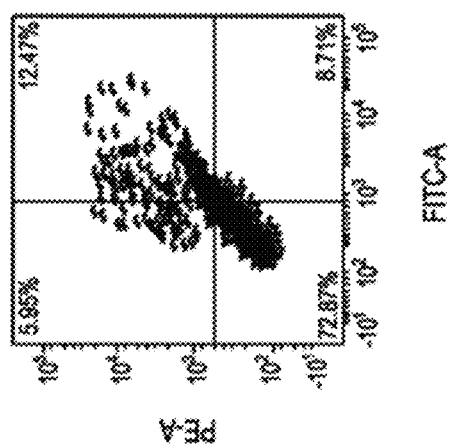
Figure 4E:
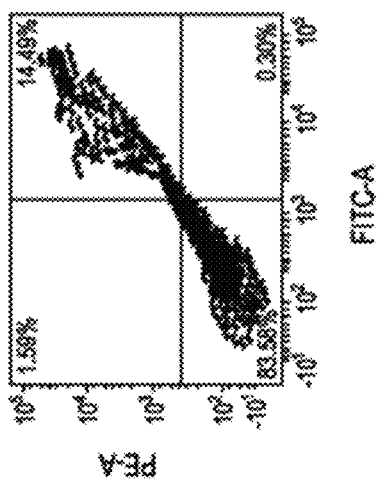

Cellular Uptake of the Liposomes of KTLLPTPK(SEQ ID NO: 1)-Lipopeptide 1 in Pancreatic Cancer Cells is Selectively Mediated Via Plectin-1 Receptor To demonstrate the pancreatic cancer cell binding properties of the liposomes of KTLLPTPK(SEQ ID NO: 1)-lipopeptide of the present invention, flow cytometry based cellular uptake experiments in pan02 cells and PANC-1 cells were performed using Rhodamine-PE labeled liposomes of KTLLPTPK(SEQ ID NO: 1)-lipopeptide. Cellular uptake efficiencies were found to be considerably inhibited when cells were pre-incubated with polyclonal antibody against plectin-1(ab83497, Abchem, USA) (FIG. 3). Thus, the findings summarized in FIG. 3 confirm that formulation of KTLLPTPK(SEQ ID NO: 1)-lipopeptide of the present invention is capable of effectively delivering therapeutics to pancreatic tumors cells via plectin-1 receptor.

Combination of Curcumin and Gemcitabine Co-Encapsulated in Liposomes of KTLLPTPK(SEQ ID NO: 1)-Lipopeptide Show Synergistic Effect in Inducing Apoptosis in Pancreatic Tumor Cells To evaluate the in vitro efficiencies of liposomally encapsulated curcumin and gemcitabine in inducing apoptosis in pancreatic tumor cells, conventional Annexin V/Propidium iodide (PI) binding based flow cytometric apoptosis assay protocols were used. When curcumin and gemcitabine were both co-encapsulated in liposomes of KTLLPTPK(SEQ ID NO: 1)-lipopeptides of the present invention, the degree of apoptosis induced in tumor cells were observed to be remarkably higher than that observed in tumor cells treated with curcumin or gemcitabine individually encapsulated (i.e. not in combination) in liposomes of KTLLPTPK(SEQ ID NO: 1)-lipopeptides of the present invention (FIG. 4). Such findings in flow cytometric apoptosis assay are fully consistent with synergic effects of curcumin and gemcitabine in inducing apoptosis in pancreatic tumor (PANC-1, PAN02) cells. Importantly, no induction of apoptosis was observed in non-cancerous healthy mouse fibroblast (NIH-3T3) cells in which expression level of plectin 1 receptor is poor (compared to that in pancreatic cancer cells).

Biodistribution Profile of NIR Dye Encapsulated Plectin-1 Targeting Liposomes of KTLLPTPK(SEQ ID NO: 1)-Lipopeptide Shows Significant Binding to p Tumor Bearing C57BL/6J Mice.

Figure 6:
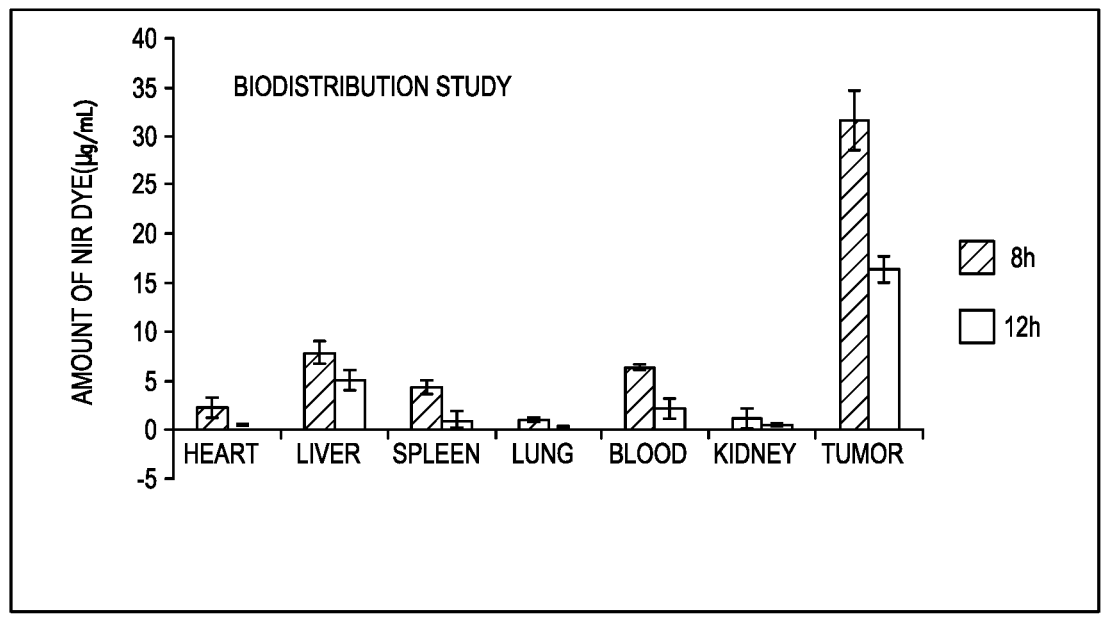
FIG. 6 shows the biodistribution profile for Plectin-1 receptor targeted cationic KTLLPTPK(SEQ ID NO: 1)-lipopeptide-1 in Pan02 Tumor bearing C57BL6/J mice

To evaluate the targeting effect KTLLPTPK(SEQ ID NO: 1)-lipopeptide 1 in a syngeneic mouse tumor model, liposomally encapsulated NIR Dye (DyLight 730-B1, Thermo scientific, USA) (2 mg/kg of body weight) was intravenously administered in C57BL/6J (n=2) mice bearing pancreatic tumors after 22 days post tumor implantation. After 8 h and 24 h post injection organs (tumor, blood, heart, lung, Liver, Kidney and spleen) were collected and homogenized in vivo lysis buffer. The NIR Dye was extracted in ethyl acetate; the ethyl acetate extract was dried and dissolved in methanol (300 µL). 100 µL duplicate was taken in 96 well plate and the florescence readings were measured at 650 and 730 nm. NIR Dye concentrations were quantified (FIG. 6) by fluorescence measurements. To correct for auto fluorescence, untreated control tissues were similarly extracted. For each sample, the background fluorescence was subtracted and the remaining counts were converted to concentration of NIR Dye using standard graph of fluorescence vs NIR Dye concentration. The findings summarized in FIG. 6 convincingly demonstrate the effectiveness of the liposomes of KTLLPTPK(SEQ ID NO: 1)-lipopeptides for delivering potent therapeutics selectively to pancreatic tumor tissues in mice bearing orthotopic pancreatic tumor.

Figure 7:
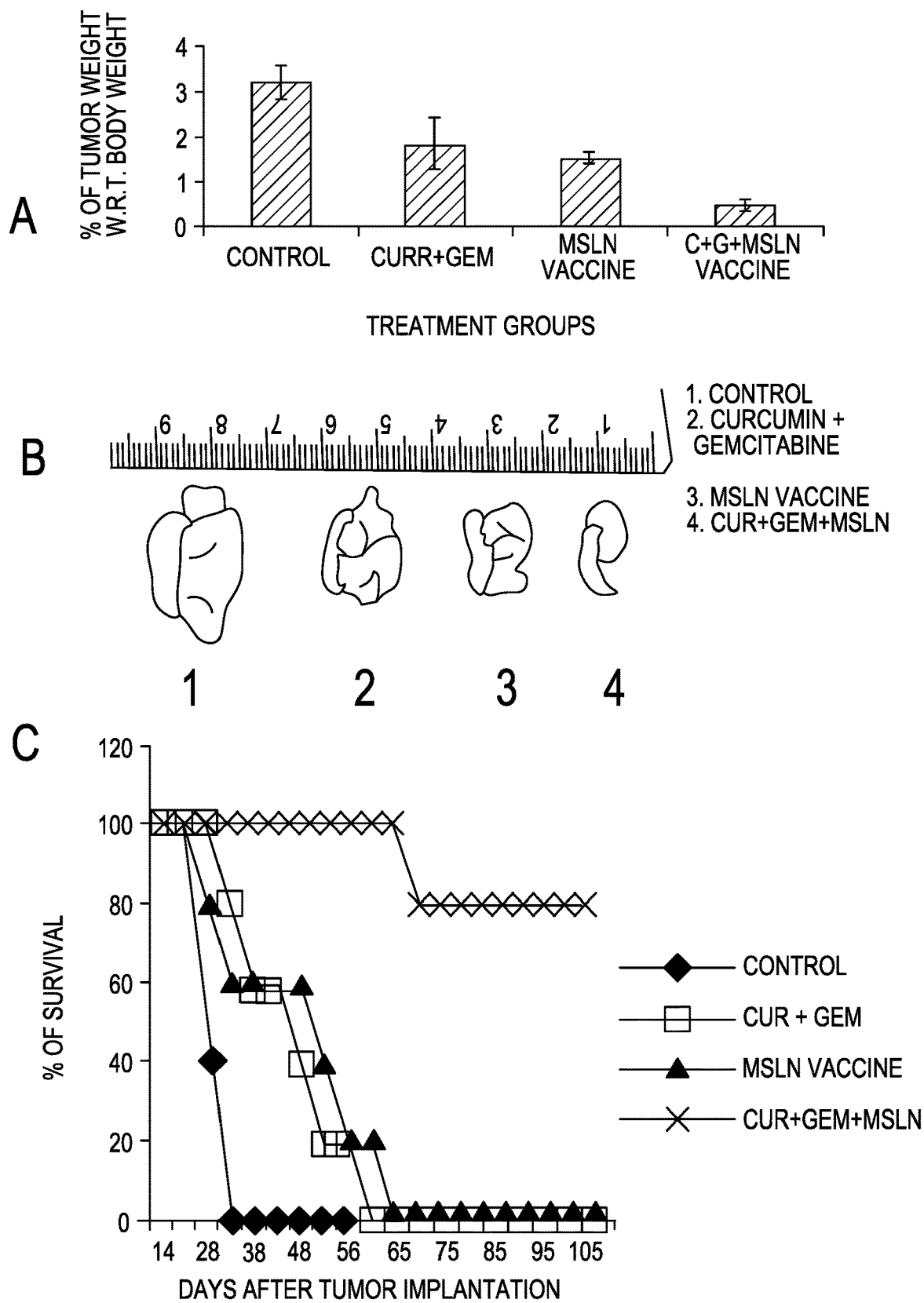
FIG. 7 shows enhanced tumor growth inhibition and survivability in tumor bearing mice upon injected with liposomal formulations containing both curcumin & gemcitabine. (A) Relative tumor growth inhibition properties by weight of targeted liposomal formulations 2. Only chemotherapy (curcumin & gemcitabine) 3. Only immunotherapy (with lipoplexes of p-CMV-MSLN and liposomes of lysinylated cationic amphiphile with guanidine & mannose-mimicking shikimoyl head-groups), 4. Both chemotherapy (curcumin & gemcitabine) and immunotherapy (with lipoplexes of p-CMV-MSLN and liposomes of lysinylated cationic amphiphile with guanidine & mannose-mimicking shikimoyl head-groups). (B) Representative tumor sizes in each group on day 30 post tumor inoculation. (C) Day 28 onwards mice were subjected for survival study.
Figure 8A:
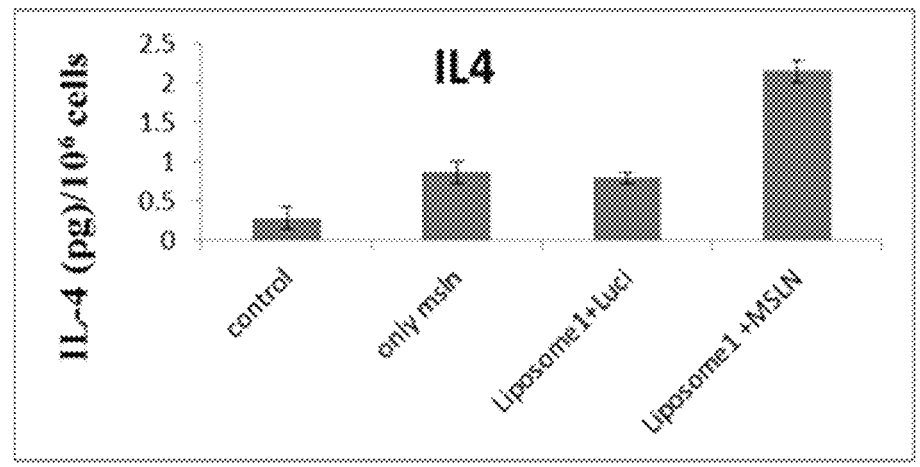
FIG. 8A-8C shows that co-culture of splenocytes (isolated from mice immunized with lipoplexes of in vivo DC-targeting lipid 1 & p-CMV-MSLN (Catalog No. SC110135, OriGene, USA) with target Pan02 cells leads to effective lysis of target cells via cell specific CTL response (A), secretion of IFN-γ (B) and IL-4 (C).
Figure 8B:
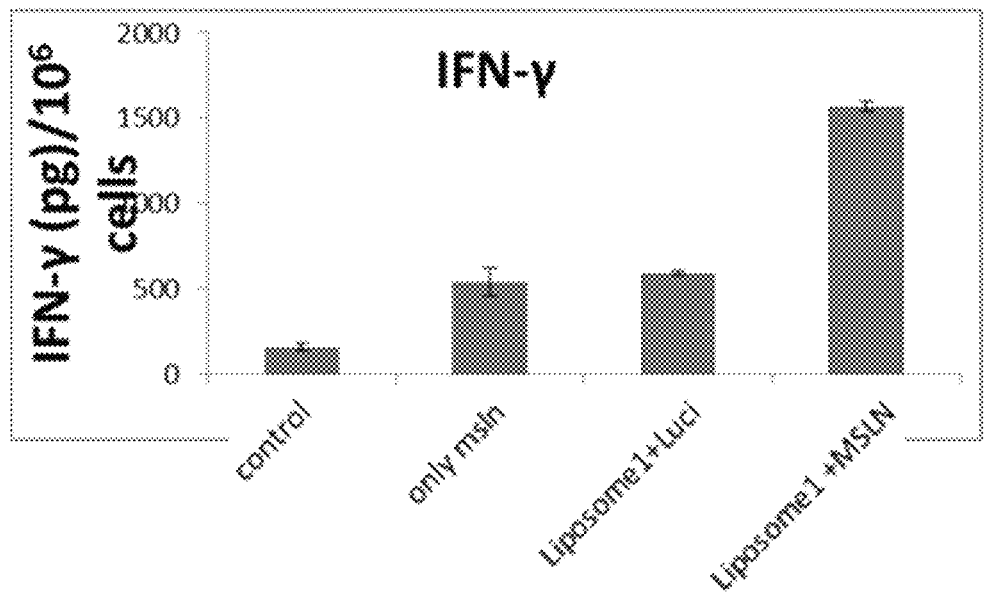
Figure 8C:
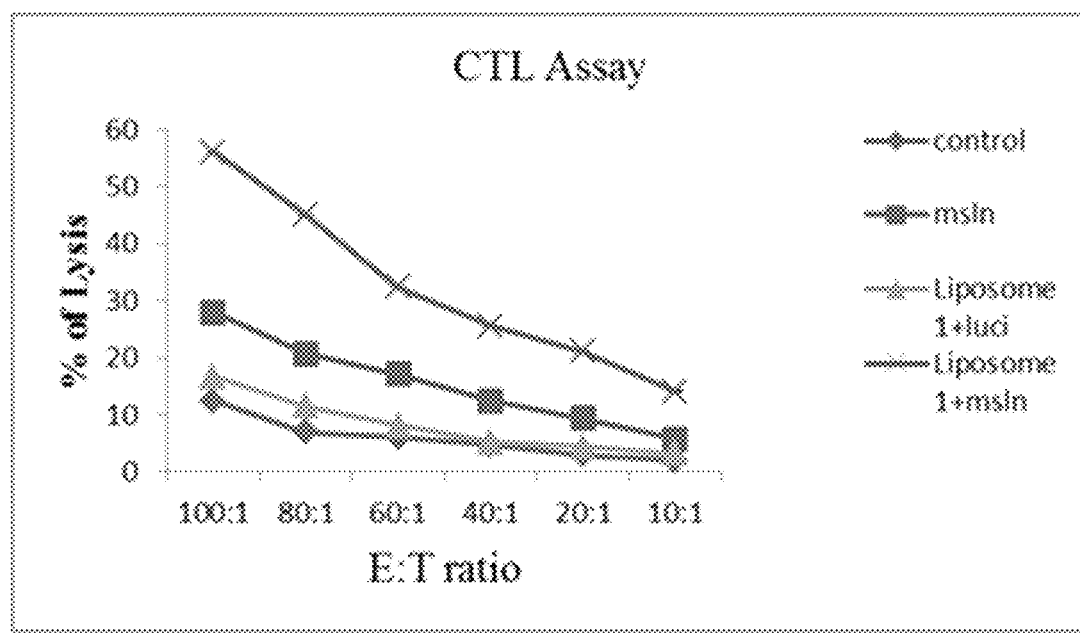

Simultaneous Application of Targeted Chemotherapy and Cancer Immunotherapy to Inhibit and Increase the Survival of Established Pancreatic Cancer Tumor in Syngeneic Mouse Tumor Model To examine the efficiency of combined therapeutic modality (i.e. simultaneous application of targeted chemotherapy and cancer immunotherapy), mice were subcutaneously immunized with mesothelin encoded DNA vaccine (p-CMV-MSLN, electrostatically complexed with direct in vivo DC-targeting liposomes of lipid 1 containing guanidine and mannose-mimicking shikimoyl head-groups via a lysine spacer in its head-group region (using 200 µL 5% glucose solution containing 15 µg p-CMV-MSLN, 4:1 lipid:DNA mole ratio for each mice) on day 3, 10 and 16 after tumor implantation. The findings summarized in FIG. 7 show genetic immunization alone (i.e. without using therapeutic agents in combination) and targeted chemotherapy (intravenous administration of curcumin (8 mg/kg B.W of mice) and gemcitabine (2 mg/kg B.W of mice) co-encapsulated in liposomes of KTLLPTPK(SEQ ID NO: 1)-lipopeptide of the present invention on day 6, 8, 12, 14 and 20 post tumor inoculation) alone were not capable of regressing established tumor growth. Importantly, targeted intravenous administration of curcumin (8 mg/kg B.W of mice) and gemcitabine (2 mg/kg B.W of mice) co-encapsulated in liposomes of KTLLPTPK(SEQ ID NO: 1)-lipopeptide of the present invention in combination with subcutaneous genetic immunization with lipoplexes of the mesothelin encoded DNA vaccine (p-CMV-MSLN) in complexation with direct in vivo mouse DC-targeting liposomes of lipid 1 was capable of providing complete regression of established tumor (FIG. 7) thereby demonstrating the remarkable therapeutic potential of such combination therapy in combating pancreatic cancer.

In summary, the ingredients of liposomal formulation of the present invention for targeted chemotherapy include plectin-1 receptor selective novel lipopeptide comprising plectin-1 targeting KTLLPTPK(SEQ ID NO: 1)-octapeptide head-group and a long aliphatic hydrocarbon chain, at least one co-lipid, potent therapeutic agents (curcumin and gemcitabine, co-encapsulated within the liposomes of KTLLPT-PK(SEQ ID NO: 1)-lipopeptide). The liposome of KTLL-PTPK(SEQ ID NO: 1)-lipopeptide of the present invention can target anticancer genes/drugs to pancreatic tumor or tumor cells via plectin-1 receptor. The findings disclosed herein demonstrate that intravenous administration of liposomal formulation of the KTLLPTPK(SEQ ID NO: 1)-lipopeptide containing encapsulated potent cytotoxic drugs such as curcumin and gemcitabine leads to significant tumor growth inhibition in a syngenic mouse tumor model by inducing apoptosis in tumor cells. Importantly, when mice receiving the liposomal formulation of the present invention for targeted chemotherapy were simultaneously immunized with an electrostatic complex of direct in-vivo dendritic cell (DC) targeting liposomes of lipid 1 & DNA vaccine encoding mesothelin (genetic immunization), established pancreatic tumor was completely regressed in 4 out of 5 treated mice. The combined therapeutic modality disclosed herein thus holds the potential of becoming a platform technology for combating various dreadful cancers.

EXAMPLES

The following examples are given by of illustrating the present invention and should not be construed to limit the scope of the invention Example 1

Synthesis of KTLLPTPK(SEQ ID NO: 1)-Lipopeptide 1

Fmoc strategy based solid phase peptide synthesis procedure was employed for preparing the cationic lipopeptide with plectin-1 targeting KTLLPTP(SEQ ID NO: 3)-head group as depicted schematically in Scheme 1. 500 mg of H-Lys(Boc)-2-C1Trt resin-1 (N$^c$—Boc-Lysine pre-loaded 2-chloro trityl resin, 0.77-0.79 mmol/g loading) was first swelled in 10 mL DMF for 4 h and then coupled with Fmoc-Pro-OH (2 equiv) using HBTU) (2 equiv) and DIPEA (4 equiv) in 10 mL DMF at room temperature for 1.5 h to afford intermediate 2. The resin was then washed with 5 mL DMF and the Fmoc group was removed with a solution of piperidine:DMF (1:4, v/v, 10 mL, 5 min, 2 times) at room temperature. Following the same Fmoc strategy, sequential couplings of Fmoc-Thr(O-tert-butyl)-OH, Fmoc-Pro-OH, Fmoc-Leu-OH, Fmoc-Leu-OH, Fmoc-Thr(O-tert-butyl)-OH and Boc-Lys(Boc)-OH (2 equiv each) using HBTU (2 equiv) and DIPEA (4 equiv) in 10 mL DMF at room temperature for 1.5 h for each amino acid afforded the resin associated octapeptide intermediate 3 (Scheme 1). The resin-bound octapeptide intermediate 3 (scheme 1) was taken out of the reaction vessel in 10 mL DCM, washed thoroughly with DCM (5×10 mL) and dried well. The resulting dried resin bound intermediate was treated with 100 mL 0.5% (v/v) TFA in DCM for 2 h at 0° C. to obtain protected octapeptide intermediate 4 (Scheme 1) (0.38 g, 76% yield). N, N-di-n-octadecyl-N-2-aminoethylamine (0.32 g, 0.57 mmol) was dissolved in dry DCM (3 mL) and the solution was added to an ice-cold reaction mixture (which has been under stirring conditions for 30 min) containing HBTU (0.22 g, 0.57 mmol), and DIPEA (99 µL, 0.57 mmol) and the protected octapeptide intermediate 4 (Scheme 1) (0.50 g, 0.38 mmol) in dry DCM (5 mL). The resulting solution was left under stirring at room temperature for 12 h. The solvent was then evaporated in the rotary evaporator at 30° C. and the residue was dried completely under high vacuum. The dried intermediate was treated with TFA:DCM (90:5 v/v, 2 mL) for 3 h at 0° C. and washed with TFA:DCM (1:9, v/v, 10 mL). The acid washings were concentrated to about 1 mL and 14 mL acetone was added until a white precipitate separated. Precipitation repeated five times with acetone and two times with 14 mL diethyl ether. The precipitate upon chloride ion exchange chromatography over 5 g of Amberlyst IRA-400 resin followed by purification with reversed phase HPLC afforded the pure KTLLPTPK(SEQ ID NO: 1)-lipopeptide 1 as a white, fluffy solid (231 mg, 48% yield based on octapeptide intermediate 4 shown in Scheme 1). The purified KTLLPTPK(SEQ ID NO: 1)-lipopeptide 1 was characterized by its molecular ion peak in ESIMS and its purity was confirmed by reversed phase analytical HPLC using two different mobile phases. ESIMS: m/z=1444 [M+1]

Example 2

Synthesis of SNLHPSDK(SEQ ID NO:2)-Lipopeptide 2

Fmoc strategy based solid phase peptide synthesis procedure was employed for preparing the non-targeting control SNLHPSDK(SEQ ID NO:2)-lipopeptide 2 as depicted schematically in Scheme 2. 500 mg of H-Lys(Boc)-2-C1Trt resin-1 (N$^c$—Boc-Lysine pre-loaded 2-chloro trityl resin, 0.77-0.79 mmol/g loading) was first swelled in 10 mL DMF for 3 h and then coupled with Fmoc-Asp(O-tert-butyl) (2 equiv) using HBTU (2 equiv) and DIPEA (4 equiv) in 10 mL DMF at room temperature for 1.5 h to afford intermediate 2 (Scheme 2). The resin was washed with 10 mL DMF and the Fmoc group was removed with a solution of piperidine:DMF (1:4, v/v, 10 mL, 5 min, 2×) at room temperature. Following the same Fmoc strategy, sequential couplings of Fmoc-Ser(O-tert-butyl)-OH, Fmoc-Pro-OH, Fmoc-His(Trt)-OH, Fmoc-Leu-OH, Fmoc-Asn(Trt)-OH and Boc-Ser(O-tert-butyl)-OH (2 equiv each) using HBTU (2 equiv) and DIPEA (4 equiv) in DMF at room temperature for 1.5 h for each amino acid afforded the resin associated octapeptide intermediate 3 (Scheme 2). The resin-bound octapeptide intermediate 3 (Scheme 2) was taken out of the reaction vessel in 10 mL DCM, washed thoroughly with DCM (5×10 mL) and dried well. The resulting dried resin bound intermediate 3 (Scheme 2) was treated with TFA:DCM (5:95, v/v, 100 mL) for 2 h at 0° C. to obtain a protected octapeptide intermediate 4 (0.37 g, 75% yield). N, N-di-n-octadecyl-N-2-aminoethylamine (0.08 g, 0.15 mmol) was then dissolved in 3 mL dry DCM and the solution was added to an ice cold reaction mixture which has been under stirring for 30 min containing EDCI (0.043 g, 0.23 mmol), HOBT (0.034 g, 0.23 mmol), DIPEA (131 µL, 0.75 mmol) and the protected octapeptide intermediate 4 (0.33 g, 0.19 mmol) in dry DCM (5 mL). The resulting solution was left under stirring at room temperature for 12 h. The solvent was then evaporated in the rotary evaporator at 30° C. and the residue was dried completely under high vacuum. The dried intermediate was treated with TFA:DCM:TIS (90:5:5 v/v, 2 mL) for 3 h at 0° C. and washed with TFA:DCM (1:9, v/v, 10 mL). The acid washings were concentrated to about 1 mL and 14 mL acetone was added until a white precipitate separated. Same precipitation process was repeated five times with 14 mL acetone each time and the final precipitate was washed two times with 14 mL of diethelyether each time. The precipitate upon chloride ion exchange chromatography over 5 g Amberlyst IRA-400 resin followed by purification with reversed phase HPLC afforded the pure SNLHPSDK(SEQ ID NO:2)-lipopeptide 2 as a white, solid (188 mg, 47% yield based on octapeptide intermediate 4 shown in Scheme 2). The purified SNLHPSDK(SEQ ID NO:2)-lipopeptide 2 was characterized by the molecular ion peak in ESIMS and purity was confirmed by reversed phase analytical HPLC using two different mobile phases. ESIMS: m/z=1444 [M+1]

Example 3

Cellular Uptake of the Liposomes of KTLLPTPK(SEQ ID NO: 1)-Lipopeptide 1 in Pancreatic Cancer Cells is Selectively Mediated Via Plectin-1 Receptor Preparation of Liposomally Encapsulated Rhodamine-PE Lipopeptides, co-lipids (DOPC, cholesterol and DSPE (SEQ ID NO: 6)-(PEG)$_{2000}$-NH$_2$) and Rhodamine-PE (at 0.5:1:0.25:0.02:0.1 molar ratios) were dissolved in chloroform methanol mixture (1:1, v/v). The mixture was then evaporated under a thin stream of nitrogen gas, vacuum dried for 8 h and hydrated in deionized water for overnight to obtain a hydrated lipid film with a final lipid concentration of 1 mM. The hydrated lipid film was first vortexed for 5 min, bath sonicated for 4 min and then frozen and thawed 10 times at −78° C. Unentrapped Rhodamine-PE was separated by using centrifugation for 15 min at 10000 rpm to remove unencapsulated Rhodamine-PE. Concentration of liposomally entrapped Rhodamine-PE was determined (at 560 and 583 nm) by fluorescence intensity measurements using a standard graph constructed from pure Rhodamine-PE samples Plectin-1 Receptor Selectivity Studies.

PANC-1, Pan02 and NIH-3T3 cells were seeded at a density of ~1.5×10$^5$ cells per well in a 6-well plate containing RPMI-1640 media with 10% FBS (v/v) for 18-24 h before treatment. The cells were separately treated with 0.1 mole % Rhodamine-PE labeled liposomes of KTLLPTPK (SEQ ID NO: 1)-lipopeptide 1. After 4 h incubation at 37° C., the cells were washed with phosphate buffer saline and the degree of cellular uptakes were measured with a flow cytometer (BD FACS Canto II) using 560 nm and 583 nm as excitation and emission wavelengths, respectively. Degrees of cellular uptake for RhPE-labeled liposomes of KTLLPTPK(SEQ ID NO: 1)-lipopeptide 1 in pancreatic cells were found to be significantly higher than those for RhPE-labeled non-targeting liposomes of SNLHPSDK(SEQ ID NO:2)-lipopeptide 2 (FIG. 3). Importantly, degree of cellular uptake for liposomes of RhPE-labeled liposomes of KTLLPTPK(SEQ ID NO: 1)-lipopeptide 1 was found to be significantly less in non-cancerous healthy mouse fibroblast (NIH3T3) cells (FIG. 3). Toward probing whether or not cellular uptake of the pancreatic cancer targeting liposomes of KTLLPTPK(SEQ ID NO: 1)-lipopeptide 1 is mediated via plectin-1 receptor, the cells were pre-incubated with 500 μL monoclonal antibody against plectin-1 (at a dilution of 1:100 in RPMI-1640 containing 10% FBS (v/v) for 2 h at room temperature. After 2 h, media was taken out and a fresh 1 mL of media containing 0.1 mole % RhPE-labeled liposomes of KTLLPTPK(SEQ ID NO: 1)-lipopeptide 1 was added to the cells. Cells were then incubated for 4 h and the degree of cellular uptake for RhPE-labeled liposomes of KTLLPTPK(SEQ ID NO: 1)-lipopeptide 1 was measured by flow cytometer. The degrees of cellular uptake in cells pre-treated with monoclonal antibody against plectin 1 receptor were found to be adversely affected compared to degrees of cellular uptake in untreated cells (FIG. 3). Such findings are fully consistent with the supposition that the liposomes of the KTLLPTPK(SEQ ID NO: 1)-lipopeptide 1 enter pancreatic cancer cells via plectin-1 receptors.

Example 4

Process for Co-Encapsulating Curcumin and Gemcitabine in the Liposomal Formulation of Lipopeptides.

The liposomal formulations of KTLLPTPK(SEQ ID NO: 1)-lipopeptide 1 and control non-targeting SNLHPSDK (SEQ ID NO:2)-lipopeptide 2 were prepared using DOPC, cholesterol and DSPE(SEQ ID NO: 6)-(PEG)$_{2000}$-NH$_2$ as co-lipids wherein the mole ratio of the lipopeptide:DOPC: cholesterol:DSPE(SEQ ID NO: 6)-(PEG)$_{2000}$-NH$_2$ are 0.5: 1:0.25.:0.02. To prepare liposomal formulation containing curcumin, curcumin stock solution was prepared by dissolving curcumin in a mixture of chloroform and methanol (1:1, v/v) in a vial. The final total lipid:curcumin ratio (w/w) used in preparing the liposomal formulations containing only curcumin and formulation containing both curcumin & gemcitabine was 10:1 for both in vitro and in vivo experiments. The solvents were removed with a thin flow of moisture free nitrogen gas and the dried lipid film was kept under high vacuum for 8 h. In case of liposomal curcumin, sterile deionized water was added. In case of liposomal gemcitabine and liposome containing both curcumin & gemcitabine, 100 mM citric acid (pH 4.0) was added to the vacuum dried lipid films and the liposomes were allowed to swell overnight. The vials were then vortexed for 2-3 min at room temperature to produce multilamellar vesicles (MLVs). MLVs were then frozen and thawed 10 times at −78° C. MLVs were then sonicated in an ice bath until clarity using a Branson 450 sonifier at 100% duty cycle and 25 W output power to produce small unilamellar vesicles (SUVs).

Curcumin-loaded liposomes were finally centrifuged for 15 min at 10000 rpm to remove unencapsulated curcumin. The amounts of liposomally entrapped curcumin were measured spectrophotometrically at 450 nm (absorbance maximum of curcumin) after lysing the liposomal solutions with 1% Triton-X. For the entrapment of gemcitabine, transmembrane pH gradients were established by passing the small unilamellar vesicles (SUVs) over a Sepharose-4B gel column equilibrated in 20 mM HEPES, 150 mM NaCl (pH 7.4). Appropriate amounts of gemcitabine was then added from a stock of gemcitabine in 150 mM NaCl and incubated with the SUVs at 60° C. for 60 min with occasional vortex. The 60° C. incubation is necessary for rapid and complete entrapment of gemcitabine inside the aqueous compartments of liposomes (no gemcitabine was detected in the pass through fraction during the amicon centrifugation of the resulting liposomal formulations). The amounts of liposomally entrapped gemcitabine were measured using HPLC at 268 nm (absorbance maximum of gemcitabine) after lysing the liposomal solutions with 1% Triton-X.

Example 5

Liposomally Co-Encapsulated Curcumin and Gemcitabine Show Synergistic Effect in Inducing Apoptosis of Pancreatic Cancer Cells.

PANC-1, Pan02 and NIH-3T3 cells were seeded at a density of ~1.5×10$^5$ cells/well in a 6 well plate and cultured for 18-24 h. Pan02 and NIH-3T3 Cells were then treated for 4 h with: (B) curcumin (4 μM) solubilized in liposomes of KTLLPTPK(SEQ ID NO: 1)-lipopeptide 1; (C) gemcitabine (200 nM) encapsulated in liposomes of KTLLPTPK(SEQ ID NO: 1)-lipopeptide 1; (D) both curcumin (2 μM) and gemcitabine (100 nM) encapsulated in liposomes of KTLLPTPK(SEQ ID NO: 1)-lipopeptide 1; and (E) both curcumin (2 μM); and gemcitabine (100 nM) co-encapsulated in non-targeting control liposomes of SNLHPSDK(SEQ ID NO:2)-lipopeptide 2. PANC-1 Cells were then treated for 4 h with: (B) curcumin (8 μM) solubilized in liposomes of KTLLPTPK(SEQ ID NO: 1)-lipopeptide 1; (C) gemcitabine (1000 nM) encapsulated in liposomes of KTLLPTPK(SEQ ID NO: 1)-lipopeptide 1; (D) both curcumin (4 μM) and gemcitabine (500 nM) encapsulated in liposomes of KTLL-PTPK(SEQ ID NO: 1)-lipopeptide 1; and (E) both curcumin (4 μM); and gemcitabine (500 nM) co-encapsulated in non-targeting control liposomes of SNLHPSDK(SEQ ID NO:2)-lipopeptide 2, An untreated cell (A) was used as control. In all the cases (A)-(E), the final volume of the complete media (RPMI-1640 containing 10% FBS, v/v) was 1.5 mL. After 4 h of incubation at 37° C., the media was replaced with 2 mL fresh complete medium and incubated for additional 24 h. Cells were then trypsinized, washed with PBS, centrifuged and the pellet was resuspended in 200 μL binding buffer containing Annexin-V FITC (0.25 μg) and Propidium iodide (PI) (1.0 μg). The mixture was then incubated for 15 min in dark and analyzed by flow cytometer (BD FACS Canto II). The degrees of apoptosis induced in pancreatic tumor cells were observed to be significantly higher when cells were treated with plectin 1 targeting liposomes of KTLLPTPK(SEQ ID NO: 1)-lipopeptide 1 containing co-encapsulated curcumin & gemcitabine compared to those for cells treated with liposomes of KTLLPTPK(SEQ ID NO: 1)-lipopeptide 1 containing only curcumin and only gemcitabine (FIG. 4). Degree of apoptosis induced was also found to be low in cells treated with non-targeting control liposomes of SNLHPSDK(SEQ ID NO:2)-lipopeptide 2 containing co-encapsulated curcumin & gemcitabine (FIG. 4). Such findings are consistent with synergistic effects of curcumin & gemcitabine in inducing apoptosis in pancreatic tumor (Pan02 and PANC-1) cells. Importantly, induction of apoptosis observed in non-cancerous healthy mouse fibroblast (NIH-3T3) cells was insignificant compared to that in pancreatic cancer cells (FIG. 4).

Example 6

Synergy Between Plectin 1 Targeted Chemotherapy & In Vivo Dendritic Cell Targeted Genetic Immunization Regresses Established Pancreatic Tumor in Syngeneic Orthotopic Mouse Tumor Model.

Figure 5:
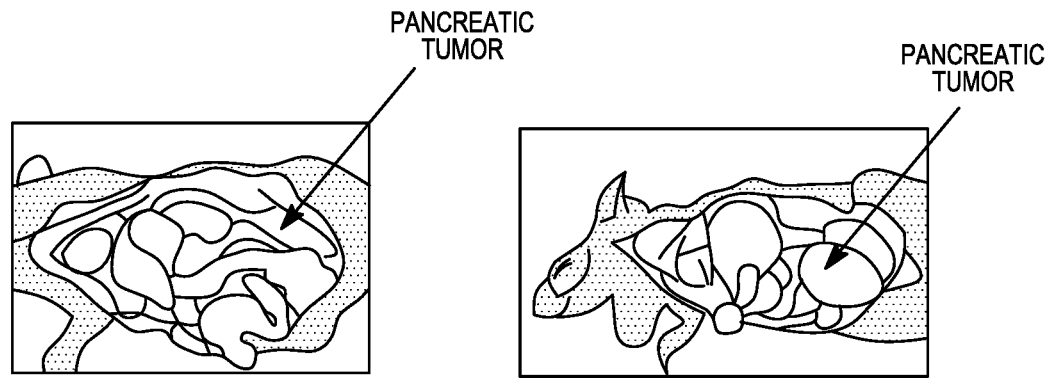
FIG. 5 shows a representative picture of orthotopic pancreatic tumor developed in C57BL6/J (CCMB, Hyderabad, India) syngeneic mice on 22 days post Pan02 cells inoculation.

In C57BL/6J mice (6-8 weeks old): Sub-confluent cultures of mouse pancreatic tumor (Pan02) cells were harvested using a 0.05% trypsin solution, washed twice with PBS and resuspended in HBSS. Cell Counting was done with heamocytometer. General anesthesia in mice was induced by I.P. injection using a combination of ketamine hydrochloride and xylometazoline hydrochloride at concentrations of 87 mg/kg body weight and 13 mg/kg body weight, respectively. The abdominal cavity was opened by a 1.5 cm wide transverse laparotomy pointing slightly to the right. The head of the pancreas was identified and lifted up by a cotton wool tip. Tumor cells (~5×10$^5$) suspended in 50 μL HBSS containing 10 μL of ice-cold Matrigel™ (BD Bioscience, a José, Calif., USA) were slowly injected into the head of the pancreas using a pre-cooled 27-gauge needle and a calibrated special syringe. Matrigel possesses watery consistency at 4° C. which turns into a gel-like substance upon reaching temperature ≥22° C. It was used to prevent local spread and thereby the early development of local peritoneal tumor growth. To further prevent leakage, a cotton wool tip was pressed onto the injection site for 30 s. The pancreas was then placed back into the abdominal cavity. The abdominal cavity was closed by a running single-layer polyester suture. To decrease postsurgical pain and the effects of surgery, betadine ointment was applied and monitored post-surgery. After 22 days mice abdominal cavity was opened and photograph (FIG. 5) of the orthotopic tumor was taken.

Following the above described procedure, orthotopic pancreatic tumors were established in 28 mice in a span of two days. On the third day, the mice were then randomly sorted into four groups (n=7 in each group). The first group was intravenously injected with vehicle (5% aqueous glucose) only on day 6, 8, 12, 14 and 20. The second group was i.v. administered with curcumin (8 mg/kg B.W of mice) and gemcitabine (2 mg/kg B.W of mice) co-encapsulated in liposomes of KTLLPTPK(SEQ ID NO: 1)-lipopeptide 1 on day 6, 8, 12, 14 and 20. The third group was only immunized with electrostatic complexes of mesothelin encoded DNA vaccine (p-CMV-MSLN) and direct in-vivo DC-targeting liposome of lipid 1 on day 3, 10 and 16 (using 200 μL 5% glucose solution containing 15 μg DNA for each mice). The fourth group was i.v. administered with plectin 1 targeting liposomes of KTLLPTPK(SEQ ID NO: 1)-lipopeptide 1 containing co-encapsulated curcumin (8 mg/kg B.W of mice) and gemcitabine (2 mg/kg B.W of mice) on day 6, 8, 12, 14 and 20. In addition, the fourth group was also immunized with electrostatic complexes (lipoplexes) of mesothelin encoded DNA vaccine (p-CMV-MSLN) and direct in-vivo DC-targeting liposome of lipid 1 on day 3, 10 and 16 (using 200 μL 5% glucose solution containing 15 μg DNA for each mice). Findings summarized in FIG. 7A convincingly demonstrated the therapeutic efficacy of combined use of targeted chemotherapy and genetic immunization in combating pancreatic cancer. FIG. 7B shows representative sizes of the tumors for all the above-mentioned mice groups measured on 30 days post of tumor cells implantation. The overall survivability data summarized in FIG. 7C clearly show that the combination of plectin 1 targeted chemotherapy and in vivo dendritic cell targeted genetic immunization described in the present invention remarkably enhances the overall survivability of mice bearing orthotopic pancreatic tumor. Collectively, the findings depicted in FIG. 7A-C demonstrate the remarkably higher therapeutic outcome of plectin 1 targeted chemotherapy in combination with in vivo dendritic cell targeted genetic immunization using liposomes of lipid 1 as DNA vaccine (p-CMV-MSLN) carrier.

Example 7

CTL Assay for Demonstrating that Immunization with In Vivo Dendritic Cell Targeting Liposomes of Lipid 1 in Complexation with Mesothelin Encoded DNA Vaccine (p-CMV-MSLN) in Pan02 Cells Induces Target Cell Selective Immune Response.

Four groups of C57BL/6J mice (each weighing 20-22 g, n=2 in each group) were subcutaneously immunized two times with seven-day intervals using 200 μL 5% glucose solution containing 15 μg DNA for each mice with: (A) electrostatic complexes (lipoplexes) of mesothelin encoded DNA vaccine (p-CMV-MSLN) and direct in vivo DC-targeting liposome of lipid 1; (B) electrostatic complexes (lipoplexes) of luciferase encoded DNA vaccine (p-CMV-luc and direct in vivo DC-targeting liposome of lipid 1 (as negative control); and (C) only mesothelin encoded DNA vaccine (p-CMV-MSLN). The fourth group (D) was not treated with anything and was used as the untreated control group. Two weeks after the second immunization, mice were sacrificed and their spleens were isolated by mincing the spleens with a syringe plunger. The viable cells were counted by hemocytometer and used for CTL assay by ELISA. Briefly, cells were seeded onto 6-well plates (~1× 10$^7$ cells/well) and co-cultured with Pan02 cells (~1×10$^6$ cells/well) in RPMI complete medium containing 100 U/mL antibiotic solution (Sigma-USA) and 50 U/ml IL-2 (Thermo Scientific, USA) for 72 h. These were then used as effector cells. Ten-thousand fresh target Pan02 cells were incubated with increasing numbers of effector cells (10:1 to 100:1) in each well of U-bottomed 96-well plates for 6 h at 37° C. in 5% $CO_2$. Lactate dehydrogenase (LDH) levels in cell culture supernatants were measured according to the manufacturer's protocol (Promega, USA). The results summarized in FIG. 7, Part C convincingly demonstrated that the group immunized with electrostatic complexes (lipoplexes) of mesothelin encoded DNA vaccine (p-CMV-MSLN) and direct in vivo DC-targeting liposome of lipid 1 were most efficient in inducing CTL response (~56% of target cell lysis) compared to all other control groups. Stated differently, the presently described in vivo DC-targeting liposomal DNA vaccine carriers are capable of inducing tumor antigen selective cellular immune response.

Example 8

IFN-γ & IL-4 Cytokine Assay for Demonstrating that Immunization with In Vivo Dendritic Cell Targeting Liposomes of Lipid 1 in Complexation with Mesothelin Encoded DNA Vaccine (p-CMV-MSLN) in Pan02 Cells Induces Majorly Cellular Immune Response.

Four groups of C57BL/6J mice (each weighing 20-22 g, n=2 in each group) were subcutaneously immunized two times with seven-day intervals using 200 µL 5% glucose solution containing 15 µg DNA for each mice with: (A) electrostatic complexes (lipoplexes) of mesothelin encoded DNA vaccine (p-CMV-MSLN) and direct in vivo DC-targeting liposome of lipid 1; (B) electrostatic complexes (lipoplexes) of luciferase encoded DNA vaccine (p-CMV-luc and direct in vivo DC-targeting liposome of lipid 1 (as negative control); and (C) only mesothelin encoded DNA vaccine (p-CMV-MSLN). The fourth group (D) was not treated with anything and was used as the untreated control group. Two weeks after the second immunization, mice were sacrificed and their spleens were isolated by mincing the spleens with a syringe plunger. The viable cells were counted by hemocytometer and used for IFN-γ and IL-4 assays by ELISA after three days stimulation with the target Pan02 cells following Manufacturer's protocol (Endogen Mouse IFN-γ Elisa kit, and mouse IL-4 Elisa kit, Pierce Biotechnology, USA). Briefly, splenocytes were incubated in 96-well plates pre-coated with anti-mouse IFN-γ or anti-mouse IL-4 antibodies (at $1 \times 10^6$ cells/well) in 50 µL complete medium, covered and incubated for 12 h at 37° C. in presence of 5% $CO_2$. The cells were washed with wash buffer (3×200 µL), 50 µL biotinylated secondary antibody added to each well and the mixture incubated for 1 h at room temperature. The plates were then washed with wash buffer (3×200 µL), incubated with 100 µL streptavidin-HRP solution for 30 min, washed again with wash buffer (3×200 µL), treated with 100 µL of TMB substrate solution and incubated for 30 min in dark. The reaction was then stopped by adding 100 µL of stop solution and the absorbance was read on a micro plate reader at 450 nm. The results summarized in FIG. 7 (Parts A & B) showed that the group immunized with electrostatic complexes (lipoplexes) of mesothelin encoded DNA vaccine (p-CMV-MSLN) and direct in vivo DC-targeting liposome of lipid 1 induced majorly cellular immune response compared to all other control groups.

Advantages of the Invention

The process of the present invention can be exploited for preparing cationic lipopeptide with plectin-1 targeting peptide head group and for delivering biologically active compounds such as DNA, RNA, potent cytotoxic drugs, proteins etc. into both tumor endothelial cells and tumor cells. The present inventions are particularly useful for plectin-1 receptor selective delivery of polyanions, polypeptides or nucleopolymers into tumor cells. The present invention describes inhibit tumor growth via by targeted delivery of curcumin and gemcitabine in pancreatic cancer tumor. The present invention demonstrates the significant therapeutic potential of using in vivo dendritic cell targeted DNA vaccination in combination with targeted chemotherapy. The present invention discloses methods for regressing established tumors by simultaneous use of targeted chemotherapy and in vivo dendritic cell targeted genetic immunization based cancer immunotherapy. Furthermore, the present invention discloses that tumor selective targeted chemotherapy can be synergized with other promising cancer immunotherapeutic modalities such as direct in vivo targeting of DNA vaccine targeting to APCs via mannose receptor in combating pancreatic cancer. The present invention describes a unique method of simultaneous use of targeted chemotherapy and cancer immunotherapy for regressing established pancreatic tumor in an orthotopic mouse tumor model. The present invention discloses method of harnessing antitumor effects by a combination of targeted chemotherapy and genetic immunization in therapeutic mode (unlike commonly used preventive mode of DNA vaccination with electrostatic complexes (lipoplexes) of DNA vaccines encoding mesothelin (p-CMV-MSLN) and direct in-vivo DC-targeting cationic liposomes. The findings disclosed in the present invention avoid the needs of: (a) toxic side effects of single chemotherapeutics; (b) painstaking isolation of autologous DCs in genetic immunization; (c) ex-vivo transfection of the isolated DCs with DNA vaccines and the reimplantation of the ex vivo transfected DCs; and (d) non-specific delivery of chemotherapeutics to other organs such as liver, spleen, kidney etc. Taken together, the liposomal formulations of the present invention can regress established tumor through combined use of targeted chemotherapy and direct in-vivo stimulation of immune systems against growing tumor.

We claim:

1. A method of regressing pancreatic tumor of a subject, comprising:

obtaining a liposomal formulation comprising a cationic lipopeptide having formula A, a first co-lipid, a second co-lipid, a pharmaceutically acceptable carrier, and a therapeutic agent, wherein a molar ratio of the cationic lipopeptide having formula A, the first co-lipid, the second co-lipid, the pharmaceutically acceptable carrier, and the therapeutic agent is 0.5:1:0.25:0.02:1-10; and administering a therapeutically effective amount of the liposomal formulation and an in vivo dendritic cell targeting DNA vaccine comprising a plasmid cytomegalovirus encoding mesothelin (p-CMV-MSLN) to a subject in need thereof via intravenous or subcutaneous injection, wherein the formula A is

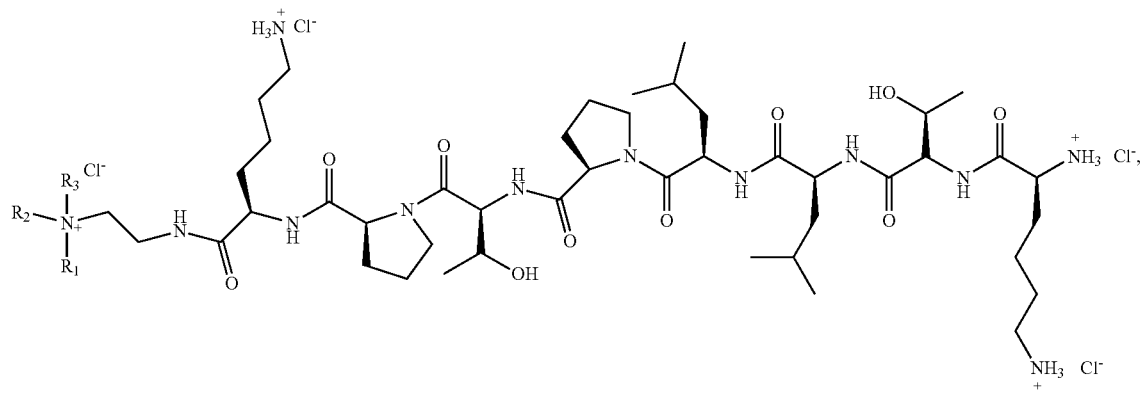

where $R_1$ and $R_2$ are each independently selected from hydrogen and a lipophilic moiety containing eight to twenty four carbon atoms selected from the group consisting of alkyl, mono-, di- and tri-unsaturated alkenyl, provided both $R_1$ and $R_2$ are not hydrogen; $R_3$ is selected from the group consisting of hydrogen, $C_1$-$C_5$ alkyl, hydroxyl, and $C_1$-$C_5$ amino-alkyl, the first and the second co-lipids are 1,2-dioleoyl-sn-glycero-3-phosphocholine (DOPC) and cholesterol, respectively, the pharmaceutically acceptable carrier is DSPE(SEQ ID NO: 6)-(PEG)$_{2000}$-NH$_2$, and the therapeutic agent is selected from the group consisting of curcumin, gemcitabine, and a combination thereof, wherein a weight ratio of curcumin to gemcitabine is 5-20:1-5 in the combination.

* * * * *